United States Patent
Kim et al.

(10) Patent No.: US 10,577,369 B2
(45) Date of Patent: Mar. 3, 2020

(54) SUBSTITUTED QUINAZOLINONES FOR INHIBITING PI3K

(71) Applicant: BIOWAY., INC, Gangwon-Do (KR)

(72) Inventors: Jongwoo Kim, Gyeonggi-do (KR); Chiwoo Lee, Gyeonggi-do (KR); Suji Hong, Gangwon-Do (KR)

(73) Assignee: BIOWAY., INC (KR)

( * ) Notice: Subject to any disclaimer, the term of this patent is extended or adjusted under 35 U.S.C. 154(b) by 0 days.

(21) Appl. No.: 16/244,368

(22) Filed: Jan. 10, 2019

(65) Prior Publication Data

US 2019/0144453 A1    May 16, 2019

Related U.S. Application Data

(63) Continuation of application No. PCT/KR2017/007535, filed on Jul. 13, 2017.

(30) Foreign Application Priority Data

Jul. 14, 2016 (KR) .......................... 10-2016-0089417
Jul. 7, 2017  (KR) .......................... 10-2017-0086691

(51) Int. Cl.
| A61K 31/517 | (2006.01) |
| C07D 239/91 | (2006.01) |
| C07D 473/34 | (2006.01) |
| A61P 1/16   | (2006.01) |
| A61P 35/02  | (2006.01) |
| A61P 35/00  | (2006.01) |
| A61P 37/00  | (2006.01) |

(52) U.S. Cl.
CPC .......... *C07D 473/34* (2013.01); *A61P 1/16* (2018.01); *A61P 35/00* (2018.01); *A61P 35/02* (2018.01); *A61P 37/00* (2018.01); *C07D 239/91* (2013.01)

(58) Field of Classification Search
CPC ..................... A61K 31/517; C07D 239/91
USPC ........................................ 514/266.3; 544/290
See application file for complete search history.

(56) References Cited

U.S. PATENT DOCUMENTS

| 8,980,901 B2    | 3/2015 | Fowler et al. |
| 10,010,550 B2   | 7/2018 | Sadhu et al. |
| 2010/0029693 A1 | 2/2010 | Douangpanya et al. |
| 2012/0015964 A1 | 1/2012 | Fowler et al. |
| 2014/0066386 A1 | 3/2014 | Gallatin et al. |
| 2014/0121224 A1 | 5/2014 | Fowler et al. |
| 2015/0087658 A1 | 3/2015 | Xi et al. |

FOREIGN PATENT DOCUMENTS

| CA | 3030692       | * | 1/2018  |
| JP | 2005-509635 A |   | 4/2005  |
| JP | 2007-537291 A |   | 12/2007 |
| JP | 2008-501707 A |   | 1/2008  |
| JP | 2012-508775 A |   | 4/2012  |
| RU | 2016-115082 A |   | 10/2017 |
| WO | WO-2005-016348 A1 | | 2/2005  |
| WO | WO-2005-016349 A1 | | 2/2005  |
| WO | WO-2005-113556 A1 | | 12/2005 |
| WO | WO-2005/120511 A1 | | 12/2005 |
| WO | WO-2006-089106 A2 | | 8/2006  |
| WO | WO-2010-057048 A1 | | 5/2010  |
| WO | WO-2013/082540 A1 | | 6/2013  |
| WO | WO-2014/023083 A1 | | 2/2014  |
| WO | WO-2015/061204 A1 | | 4/2015  |
| WO | WO-2015/191743 A1 | | 12/2015 |

OTHER PUBLICATIONS

Jordan, V. C. Nature Reviews: Drug Discovery, 2, 2003, 205.*
Hackam, et al. JAMA, 296(14), 2006, 1731-1732.*
Shah. A. et al., 'Idelalisib: a Novel PI3Kδ Inhibitor for Chronic Lymphocytic Leukemia', Annals of Pharmacotherapy, 2015, vol. 49, No. 10, pp. 1162-1170.
Office Action from corresponding Korean Patent Application No. 10-2017-0086691, dated Jun. 14, 2018.
International Search Report from corresponding PCT Application No. PCT/KR2017/007535, dated Oct. 25, 2017.
Notice of Acceptance for Patent Application in corresponding Australian Patent Application No. 2017297096, dated Feb. 28, 2019.

(Continued)

*Primary Examiner* — Douglas M Willis
(74) *Attorney, Agent, or Firm* — Harness, Dickey & Pierce, P.L.C.

(57) ABSTRACT

The present invention relates to novel quinazolinone derivatives inhibiting PI3K; a method for preparing the derivatives; and a pharmaceutical composition for treating hematologic neoplasms or liver diseases, containing the quinazolinone derivatives, wherein the novel quinazolinone derivatives according to the present invention have a beneficial effect in the treatment of hematologic neoplasms or liver diseases. Particularly, the quinazolinone derivatives inhibit PI3Kδ with high selectivity compared to that of a conventional anticancer drug of PI3Kδ inhibitors, thereby significantly reducing immunotoxicity, or simultaneously inhibit PI3Kδ and PI3Kγ, thereby enabling the treatment of autoimmune diseases, and anticancer therapy for blood cancer and the like. These targeted drugs have reduced side effects. The present invention provides a compound represented by Formula 1 or a pharmaceutically acceptable salt thereof, wherein X is —H, halogen, —CH$_3$, or —NH$_2$; and Y is C$_{1-2}$ linear alkyl or C$_{3-4}$ cycloalkyl.

[Formula 1]

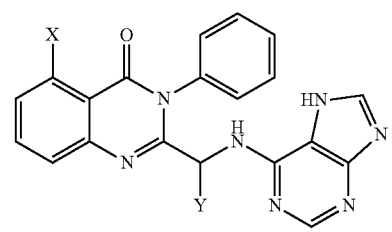

13 Claims, 8 Drawing Sheets

(56) References Cited

OTHER PUBLICATIONS

Search Report from corresponding Russian Patent Application No. 2019103684/20(006903), dated Apr. 18, 2019.
Office Action from corresponding Russian Patent Application No. 2019103684/20(006903), dated Apr. 18, 2019.
Office Action from corresponding Chinese Patent Application No. 201780043603.1, dated Jul. 24, 2019.
Office Action from corresponding Japanese Patent Application No. 2019-513840, dated Jun. 11, 2019.
Office Action from corresponding Great Britain Patent Application No. 1819957.0, dated Jun. 17, 2019.
Office Action from corresponding European Patent Application No. 17827977.4, dated Jun. 13, 2019.
Shan, A., "Idelalisib: A Novel PI3Kβ Inhibitor for Chronic Lymphocytic Leukemia", Annals of Pharmacotherapy, 2015, 49 (10), 1162-1170.
Q. Yang et al: "Idelalisib: First-in-Class PI3K Oelta Inhibitor for the Treatment of Chronic Lymphocytic Leukemia, Small Lymphocytic Leukemia, and Follicular Lymphoma", Clinical Cancer Research, vol. 21 , No. 7, Apr. 1, 2015 (Apr. 1, 2015), pp. 1537-1542, XP055305408, & Meeting of the American-Association-For-Cancer-Research (AACR) Precision Medicine Series—Integrati; Salt Lake, UT, USA; Jun. 13-16, 2015 ISSN: 1078-0432, 001: 10.1158/1078-0432.CCR-14-2034.
Notice of Allowance from corresponding Canadian Patent Application No. 3,030,692, dated Aug. 27, 2019.
First Examination Report from corresponding Indian Patent Application No. 201917001218, dated Oct. 22, 2019.
Notice of Allowance from corresponding Japanese Patent Application No. 2019-513840, dated Oct. 8, 2019.
Notice of Allowance from corresponding Great Britain Patent Application No. 1819957.0, dated Sep. 27, 2019.

* cited by examiner

Results of Single Dose Oral Toxicity Tests in Rats (Female)

| Drug \ Concentration (mg/Kg) | 100 | 300 | 900 | 1500 |
|---|---|---|---|---|
| Formula 7 | X | X | X | X |
| Formula 8 | X | X | X | Dead |

FIG. 9

SUBSTITUTED QUINAZOLINONES FOR INHIBITING PI3K

CROSS-REFERENCE TO RELATED APPLICATIONS

This application is a continuation application of PCT Application No. PCT/KR2017/007535, filed on Jul. 13, 2017, which claims the benefit and priority to Korean Patent Application Nos. 10-2016-0089417, filed on Jul. 14, 2016 and 10-2017-0086691, filed on Jul. 7, 2017. The entire disclosures of the applications identified in this paragraph are incorporated herein by references.

FIELD

The present invention relates to novel quinazolinone derivatives inhibiting PI3K and a method of preparing these derivatives.

In addition, the present invention provides a pharmaceutical composition for treating a blood cancer, a liver disease, or an autoimmune disease, which includes the quinazolinone derivatives.

BACKGROUND

Cancer is the second leading cause of death after heart disease in the United State (Cancer Facts and FIGS. 2005, American Cancer Society, Inc.). In the early stage of cancer development, a method of removing tumors or killing cancer cells by chemotherapy, radiotherapy, and the like may be selected, but in the case of terminal cancer patients, side effects due to aggressive therapies are relatively large and the response rate after treatment is low, and thus therapies for reducing side effects by delaying cancer progression and improving the quality of life may be selected. In these aspects, anticancer drugs are intended to not only prevent cancer recurrence by destroying cancer cells, but also prolong the survival period by inhibiting the growth and proliferation of cancer cells, when it is difficult to expect a full recovery.

Existing chemotherapy for metastatic cancers fail to provide long-term treatment due to their reduced efficacy. In addition, although new chemotherapies have been introduced in the medical field, there is still a need for novel effective medicines as primary, secondary and tertiary therapies in single treatment or co-treatment with existing agents, for the treatment of resistant tumors.

In addition, even anticancer drugs with strong potency are not applicable to all cancers, and thus there is an urgent need to develop medicines to improve treatment efficiency.

Targeted therapies are advantageous in that they are tumor-specific, effective, and have far less effect on normal cells compared to existing systemic anticancer treatments. The dysregulation of protein kinases is commonly found in cancer cells, and thus is an attractive target for the development of anticancer drugs.

Among lipid kinases, the structure and function of PI3Ks (phosphatidylinositol-3-kinase isomers) have been gradually and clearly verified in recent years. PI3Ks are known to belong to a family of enzymes that play a vital role in intracellular signaling pathways and are involved in major cellular functions such as cell growth, proliferation, differentiation, motility, survival, and intracellular trafficking.

Over the past 20 years, it has been steadily revealed that when PI3Ks lose their regulatory function, problems such as overactivation and the like occur in intracellular signaling pathways to induce many types of diseases.

PI3Ks are classified into Class I, Class II, and Class III. Class I is divided again into sub-classes: Class IA and Class IB. Class I PI3K is in the form of a dimer, and the dimer is divided into catalytic and regulatory subunits. Class 1A PI3K is a dimer consisting of a p110 catalytic subunit and a p85 regulatory subunit, and in this regard, the p110 catalytic subunit includes three isoforms, i.e., p110α, p110β, and p110δ. Thus, the isoforms of PI3Ks are referred to as PI3Kα, PI3Kβ, and PI3Kδ.

Meanwhile, Class IB PI3K is a dimer consisting of a p110γ catalytic subunit and a p101 regulatory subunit, and the PI3K is generally referred to as PI3Kγ.

PI3Kδ is mainly induced by receptor tyrosine kinases (RTKs) to phosphorylate PIP2 to PIP3, and PI3Kγ is mainly induced by G-protein coupled receptors (GPCRs) to phosphorylate PIP2 to PIP3. PIP3 activates protein kinase B (Akt/PKB) and continuously leads to downstream signaling, thereby being involved in major cell function regulation such as cell growth, proliferation, differentiation, motility, survival, and intracellular trafficking. It has been one of the strongest concerns of recent years that various diseases ranging from inflammation and autoimmunity to hematologic malignancy and solid cancer occur when PI3Kδ and PI3Kγ have malfunction in the regulation of intracellular signal transduction, and accordingly, there have been intensive efforts to develop drugs for treating inflammation, autoimmunity, hematologic malignancy, and solid cancer by inhibiting PI3Kδ and PI3Kγ that lose their regulatory functions.

An example of representative drugs being developed in this field is idelalisib, a substance that was developed by Gilead Calistoga and selectively inhibits PI3Kδ. This drug has excellent efficacy against various types of hematologic malignancies, and thus has drawn attention as a breakthrough drug that addresses problems (especially cytotoxicity against normal cells) of existing cytotoxic anticancer drugs and also compensates for problems of the efficacy of existing anticancer drugs. However, in Europe, some cases of serious toxicity has occurred during clinical trials, in which patients died from pneumonia, and thus the development of this drug has now been suspended. According to a report, the reason is that the inhibitory activity of this drug was sufficiently selective and potent for PI3Kδ rather than for PI3Kα and PI3Kβ, but not sufficiently selective than for PI3Kγ. Duvelisib exhibited dual-inhibitory activity on PI3Kδ and PI3Kγ and thus had a possibility of being developed as a very promising drug for treating hematologic malignancy, inflammation, and autoimmune disease. However, during clinical trials, the development of Duvelisib was terminated because of problems similar to those of idelalisib. It is known that the inhibitory efficacy of this substance is not sufficiently selective for PI3Kδ and PI3Kγ than for PI3Kβ. Therefore, there is a need to develop a drug capable of more selectively inhibiting PI3Kδ rather than at least idelalisib.

Meanwhile, quinazolinone derivatives are special structures present in many biologically active compounds such as methaqualone, which is a sedative-hypnotic drug, chloroqualone, which is an antitussive, and piriqualone, which is an anticonvulsant. Quinazolinone and derivatives thereof have a wide range of biological properties such as hypnosis, pain killing, inhibition of convulsions, inhibition of coughing, and anti-inflammatory activity.

In particular, quinazolinone derivatives are used in the treatment of cell proliferative diseases including cancer, and are one of the therapeutic agents which have been widely used recently. For example, U.S. Pat. Nos. 5,747,498 and 5,773,476 disclose quinazolinone derivatives used for the treatment of cancer which is induced by over-activation or aberrant activation of receptor tyrosine kinases. Therefore, quinazolinone derivatives are required to be studied and developed through various approaches for the treatment of cell proliferative diseases.

SUMMARY

Technical Problem

This disclosure provides novel quinazolinone derivatives that inhibit PI3Ks and methods of preparing these derivatives.

This disclosure also provides a pharmaceutical composition comprising the quinazolinone derivatives for preventing or treating a blood tumor, a liver disease, or an autoimmune disease.

Technical Solution

According to an aspect of the present application, there is provided a compound represented by Formula 1 below or a pharmaceutically acceptable salt thereof:

[Formula 1]

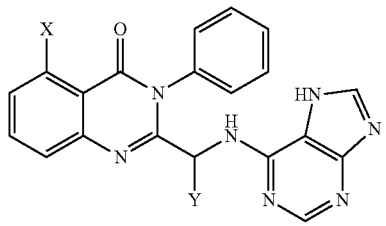

wherein,
X is —H, halo, —CH$_3$, or —NH$_2$; and
Y is C$_{1-2}$ linear alkyl or C$_{3-4}$ cycloalkyl.

According to another aspect of the present invention, there is provided a pharmaceutical composition comprising a compound represented by Formula 1 below or a pharmaceutically acceptable salt thereof as an active ingredient for preventing or treating a blood cancer, a liver disease, or an autoimmune disease.

[Formula 1]

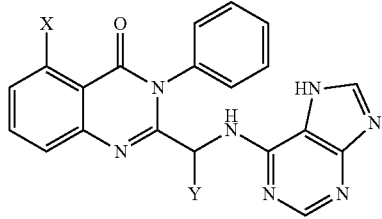

wherein,
X is —H, halo, —CH$_3$, or —NH$_2$; and
Y is C$_{1-2}$ linear alkyl or C$_{3-4}$ cycloalkyl. The blood cancer may be leukemia or lymphoma.

The liver disease may be selected from the group consisting of non-alcoholic fatty liver disease (NAFLD), non-alcoholic steatohepatitis (NASH), hepatic steatosis, hepato-cirrhosis, hepatitis, hepatic adenoma, insulin hypersensitivity, and liver cancer.

The autoimmune disease may be selected from the group consisting of allergic rhinitis, asthma, chronic obstructive pulmonary disease (COPD), and rheumatoid arthritis.

According to still another aspect of the present invention, there is provided a method of preparing a compound represented by Formula 1 below, the method including:

reacting a compound represented by Formula 2 below with a compound represented by Formula 3 below to prepare a compound represented by Formula 4 below;

deprotecting the compound represented by Formula 4 below to prepare a compound represented by Formula 5 below; and reacting a compound represented by Formula 5 below with a compound represented by Formula 6 to prepare the compound of Formula 1.

[Formula 1]

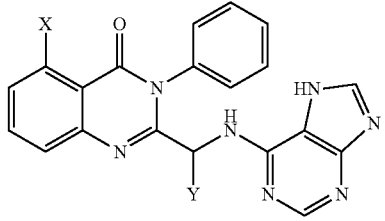

wherein, in Formula 1,
X is —H, halo, —CH$_3$, or —NH$_2$; and
Y is C$_{1-2}$ linear alkyl or C$_{3-4}$ cycloalkyl.

[Formula 2]

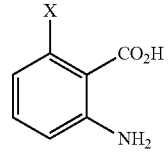

wherein, in Formula 2,
X is —H, halo, —CH$_3$, or —NH$_2$.

[Formula 3]

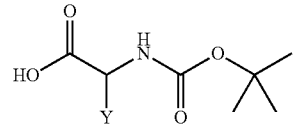

wherein, in Formula 3,
Y is C$_{1-2}$ linear alkyl or C$_{3-4}$ cycloalkyl.

[Formula 4]

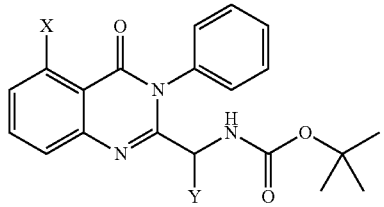

wherein, in Formula 4,
X is —H, halo, —CH$_3$, or —NH$_2$; and
Y is C$_{1-2}$ linear alkyl or C$_{3-4}$ cycloalkyl.

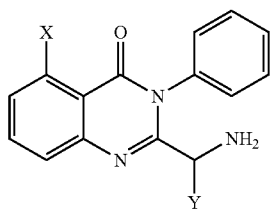
[Formula 5]

wherein, in Formula 5,
X is —H, halo, —CH$_3$, or —NH$_2$; and
Y is C$_{1-2}$ linear alkyl or a C$_{3-4}$ cycloalkyl.

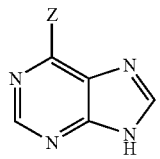
[Formula 6]

wherein, in Formula 6,
Z is halo.

Advantageous Effects

Novel quinazolinone derivatives according to the present invention are efficacious in treating blood cancer or liver diseases.

In particular, as compared to existing PI3Kδ inhibitors, the quinazolinone derivatives of the present invention can inhibit PI3Kδ with high selectivity to reduce immunotoxicity significantly, or inhibit PI3Kδ and PI3Kγ simultaneously, thus enabling not only the anticancer treatment of hematologic malignancies and the like, but also the treatment of autoimmune diseases. These targeted therapeutic agents can address problems such as side effects of existing anticancer treatments with severe cytotoxicity.

BRIEF DESCRIPTION OF THE DRAWINGS

FIG. 9 is a table for confirming toxicity according to the concentrations of a compound of Formula 7 and a compound of Formula 8 in Experimental Example 7, which is a single dose toxicity test in rats.

DETAILED DESCRIPTION

Figure 1:
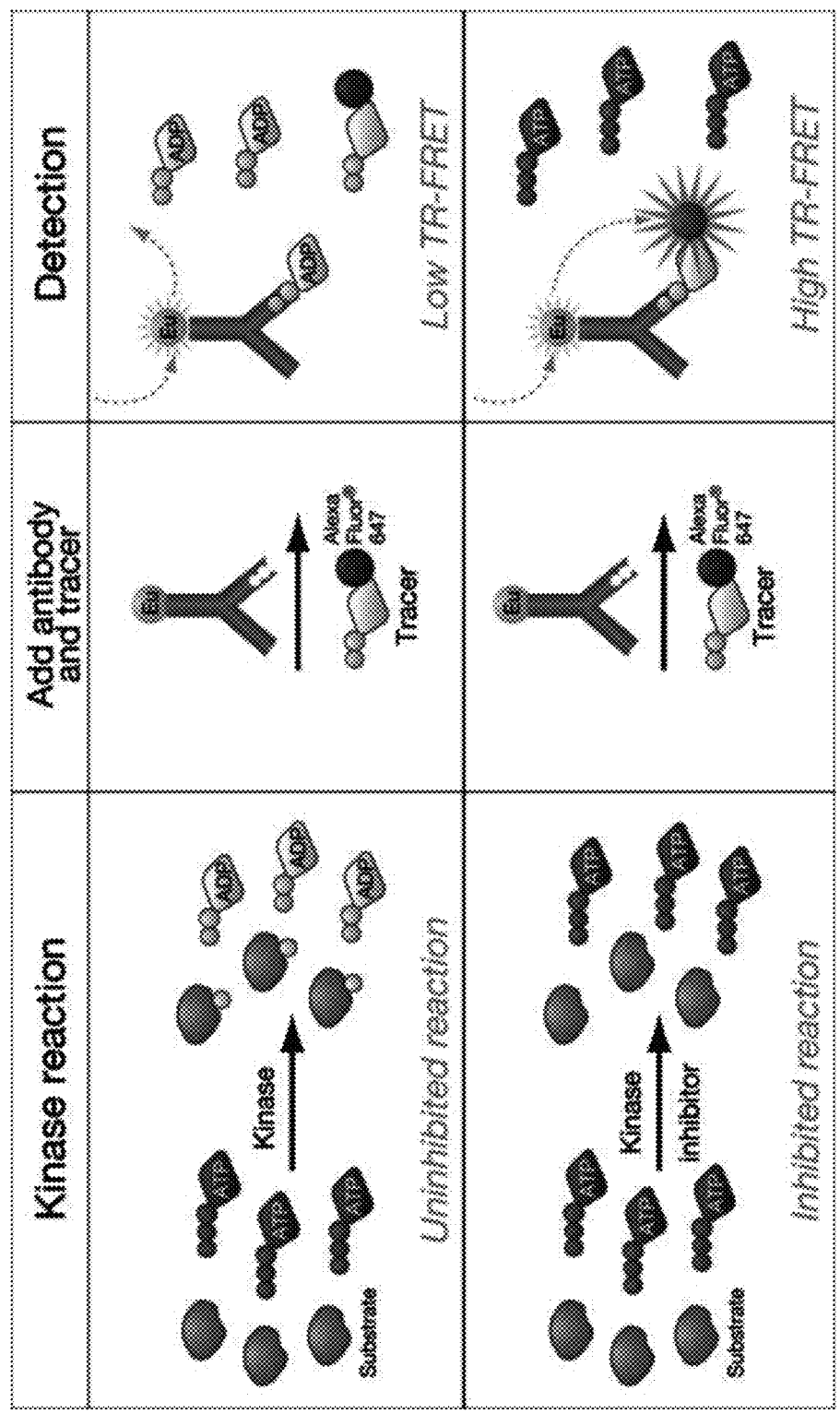
FIG. 1 illustrates the principle of an Adapta kinase analysis experiment of Experimental Example 1.

Hereinafter, the present invention will be described in detail. The terms or words used in the present specification and claims should not be construed as being limited to ordinary or dictionary meanings and should be construed as meanings and concepts consistent with the spirit of the present invention based on a principle that an inventor can appropriately define concepts of terms to explain the invention of the inventor in the best way. Thus, configurations described in embodiments set forth herein are merely exemplary embodiments of the present invention and do not represent all technical ideas of the present invention, and thus it should be understood that various equivalents and modifications that may replace these embodiments can be made at the filing time of the present application.

The present invention relates to novel compounds of quinazolinone derivatives as PI3K inhibitors. PI3K inhibitors block the PI3K-AKT signaling pathway by docking with an ATP-binding site of p110δ, and the activation of PI3K pathways is mediated by PI3K catalytic isotypes, i.e., p110α, p110β, p110δ, and p110γ.

p110δ plays a vital role in blood cancer and B cell development and is predominantly expressed in hematopoietic stem cells, and is expressed in many cancers including leukemia, lymphoma, colorectal cancer, bladder cancer, malignant glioma, and the like. It regulates cell proliferation through stimulation of related cytokines and chemokines via the PI3K-AKT signaling pathway.

In addition, novel quinazolinone derivatives according to the present invention overcome existing toxicity problems including hepatotoxicity. Since PI3K p110δ might be highly expressed even in advanced hepatocellular carcinoma, novel quinazolinone derivatives according to the present invention are also effective as a therapeutic agent for hepatocellular carcinoma, which is solid cancer.

In view of problems of existing quinazolinone-based anticancer drugs, novel quinazolinone derivatives should sufficiently and selectively inhibit PI3Kδ. Preferably, selectivity between PI3K isomers needs to satisfy the criteria that, using IC$_{50}$ values, each of ratios of PI3Kα/PI3Kδ and PI3Kβ/PI3Kδ exceeds 150, and a ratio of PI3Kγ/PI3Kδ is greater than that of idelalisib at least.

In addition, when PI3Kδ and PI3Kγ are simultaneously inhibited, it is preferable that ratios of PI3Kβ/PI3Kδ and PI3Kβ/PI3Kγ are greater than those of duvelisib.

The present invention provides a compound represented by Formula 1 or a pharmaceutically acceptable salt thereof.

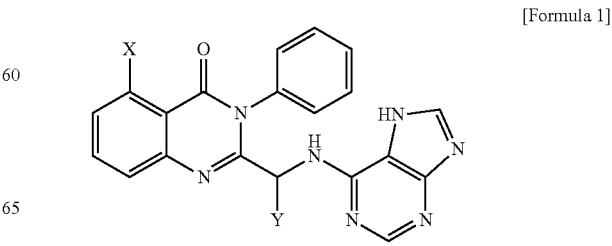
[Formula 1]

wherein,

X is —H, halo, —CH$_3$, or —NH$_2$; and

Y is C$_{1-2}$ linear alkyl or C$_{3-4}$ cycloalkyl.

The term "halo" as used herein refers to fluoro (F), bromo (Br), chloro (Cl), or iodo (I). In Formula 1, Y may be linked in the form of (S)-isomer or (R)-isomer, but preferably in the form of (S)-isomer.

Specific examples of the compound of Formula 1 include compounds represented by the following Formulas 7 to 14, but the present invention is not limited thereto.

The Compound of Formula 7 according to the present invention is the compound of Formula 1 wherein X is —F, and Y is cyclopropyl.

[Formula 7]

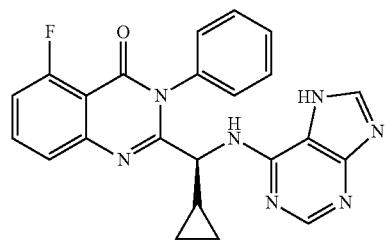

In addition, the compound of Formula 8 according to the present invention is the compound of Formula 1 wherein X is methyl, and Y is cyclopropyl.

[Formula 8]

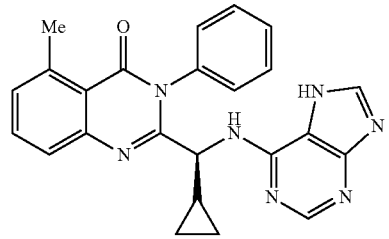

In addition, the compound of Formula 9 according to the present invention is the compound of Formula 1 wherein X is —NH$_2$, and Y is cyclopropyl.

[Formula 9]

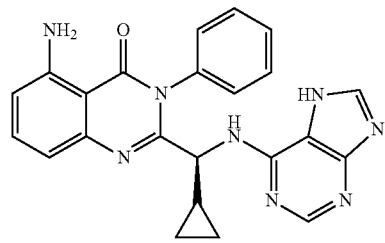

In addition, the compound of Formula 10 according to the present invention is the compound of Formula 1 wherein X is —NH$_2$, and Y is methyl.

[Formula 10]

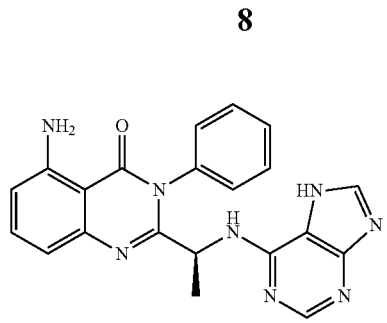

In addition, the compound of Formula 11 according to the present invention is the compound of Formula 1 wherein X is —NH$_2$, and Y is ethyl.

[Formula 11]

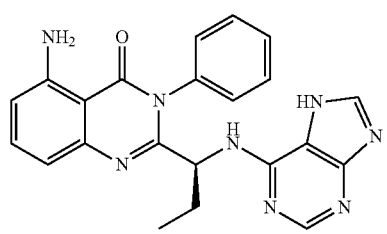

In addition, the compound of Formula 12 according to the present invention is the compound of Formula 1 wherein X is —Cl, and Y is cyclopropyl.

[Formula 12]

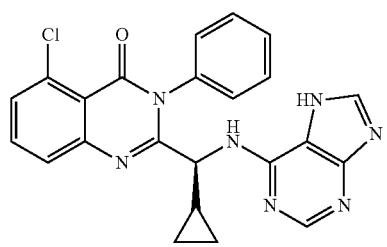

In addition, the compound of Formula 13 according to the present invention is the compound of Formula 1 wherein X is —F, and Y is cyclobutyl.

[Formula 13]

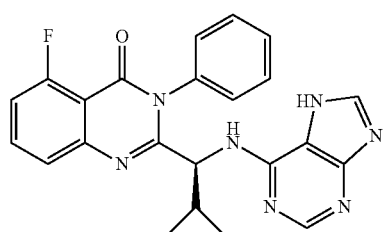

In addition, the compound of Formula 14 according to the present invention is the compound of Formula 1 wherein X is —Cl, and Y is cyclobutyl.

[Formula 14]

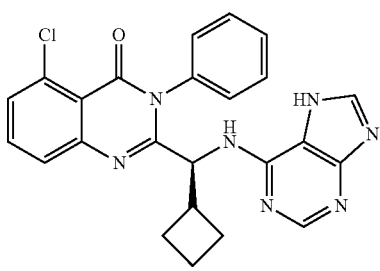

The compound represented by Formula 1 of the present invention may be used in the form of a pharmaceutically acceptable salt, and the salt may be an acid addition salt formed by a pharmaceutically acceptable free acid. The acid addition salt is obtained from: inorganic acids such as hydrochloric acid, nitric acid, phosphoric acid, sulfuric acid, hydrobromic acid, hydriodic acid, nitrous acid, phosphorous acid, and the like; nontoxic organic acids such as aliphatic mono- and dicarboxylates, phenyl-substituted alkanoates, hydroxy alkanoates and alkandioate, aromatic acids, aliphatic and aromatic sulfonic acids, and the like; or organic acids such as acetic acid, benzoic acid, citric acid, lactic acid, maleic acid, gluconic acid, methanesulfonic acid, 4-toluenesulfonic acid, tartaric acid, fumaric acid, and the like. Examples of these pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitro benzoates, hydroxybenzoates, methoxybenzoates, phthalates, terephthalates, benzenesulfonates, toluenesulfonates, chlorobenzenesulfonates, xylenesulfonates, phenyl acetates, phenylpropionates, phenylbutyrates, citrates, lactates, β-hydroxybutyrates, glycolates, malates, tartrates, methanesulfonates, propanesulfonates, naphthalene-1-sulfonates, naphthalene-2-sulfonates, mandelates, and the like.

Acid addition salts according to the present invention may be prepared using a conventional method. For example, these acid addition salts may be prepared by dissolving the derivative of Formula 1 in an organic solvent, such as methanol, ethanol, acetone, dichloromethane, acetonitrile, or the like, adding an organic acid or an inorganic acid thereto to produce a precipitate, and filtering and drying the precipitate, or may be prepared by distilling a solvent and an excess of an acid under reduced pressure and then drying the resulting solution, followed by crystallization in the presence of an organic solvent.

In addition, pharmaceutically acceptable metallic salts may be prepared by using bases. Alkali metal or alkali earth metal salts are obtained by, for example, dissolving a compound in an excess of an alkali metal hydroxide or alkali earth metal hydroxide solution, filtering an insoluble compound salt, and evaporating and drying the filtrate. At this time, it is pharmaceutically preferable that a sodium salt, a potassium salt, or a calcium salt is prepared as a metal salt. In addition, salts corresponding thereto are obtained by reacting an alkali metal or an alkali earth metal salt with a suitable silver salt (e.g., silver nitrate).

Moreover, the present invention includes not only the compound represented by Formula 1 and pharmaceutically acceptable salts thereof, but also solvates, stereoisomers, hydrates, and the like that may be prepared therefrom.

The present invention also provides a pharmaceutical composition for preventing or treating a blood cancer, a liver disease, and an autoimmune disease, which includes a compound represented by Formula 1 below or a pharmaceutically acceptable salt thereof as an active ingredient.

[Formula 1]

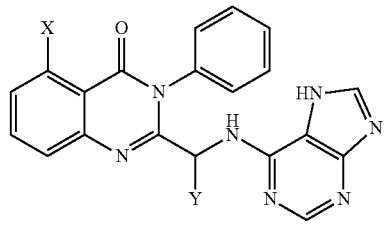

wherein,
X is —H, halo, —CH$_3$, or —NH$_2$; and
Y is C$_{1-2}$ linear alkyl or C$_{3-4}$ cycloalkyl.

In Formula 1, Y may be linked in the form of (S)-isomer or (R)-isomer, but it is preferable that Y is linked in the form of (S)-isomer. In the pharmaceutical composition according to the present invention, the compound represented by Formula 1 or a pharmaceutically acceptable salt thereof may be administered orally or parenterally in various dosage forms during clinical administration, and may be formulated using commonly used diluents or excipients such as fillers, extenders, binders, wetting agents, disintegrating agents, surfactants, and the like.

Formulations for oral administration may include, for example, tablets, pills, hard/soft capsules, liquids, suspensions, emulsions, syrups, granules, elixirs, suspensions, troches, and the like. These formulations include, in addition to the active ingredient, a diluent (e.g., lactose, dextrose, sucrose, mannitol, sorbitol, cellulose, and/or glycine) or a lubricant (e.g., silica, talc, stearic acid and magnesium or calcium salts thereof, and/or polyethylene glycol). Tablets may include a binder such as magnesium aluminum silicate, starch paste, gelatin, methyl cellulose, sodium carboxymethylcellulose, and/or polyvinylpyrrolidone, and in some cases, may include a disintegrating agent such as starch, agar, alginic acid or sodium salts thereof, or a boiling mixture and/or an absorbent, a coloring agent, a flavoring agent, and a sweetening agent.

The pharmaceutical composition including the compound represented by Formula 1 as an active ingredient may be administered parenterally, and the parenteral administration is performed via subcutaneous injection, intravenous injection, intramuscular injection, or intrathoracic injection.

In this regard, to prepare formulations for parenteral administration, the compound represented by Formula 1 or a pharmaceutically acceptable salt thereof is mixed with a stabilizer or a buffer in water to prepare a solution or a suspension, followed by preparation into an ampoule or vial unit dosage form. The composition may be sterilized and/or may include an adjuvant such as a preservative, a stabilizer, wettable powder, a salt for osmoregulation, and/or a buffer, and other therapeutically effective materials, and may be formulated using a conventional method, such as mixing, granulation, or coating.

The composition of the present invention may further include, in addition to the quinazolinone compound, one or more effective ingredients exhibiting identical or similar functions.

A suitable dose of the pharmaceutical composition of the present invention may be appropriately selected depending on the condition and body weight of patients, the severity of symptoms, the dosage form, the route of administration, and the period of administration. In the composition of the present invention, it is preferable that the effective ingredient(s) is(are) administered in an amount of 0.2 mg/kg to 200 mg/kg daily for optimum efficacy. The composition may be administered once a day or multiple doses a day, but the present invention is not limited thereto.

According to the present invention, the blood cancer may be leukemia or lymphoma.

The leukemia may be selected from acute lymphocytic leukemia (ALL), acute myelogenous leukemia (AML), chronic lymphocytic leukemia (CLL), and small lymphocytic lymphoma (SLL), and acute lymphocytic leukemia is also known as acute lymphoblastic leukemia.

The lymphoma may be a mature (peripheral) B-cell neoplasm, and more particularly, may be selected from B-cell chronic lymphocytic leukemia/small lymphocytic lymphoma; B-cell prolymphocytic leukemia; lymphoplasmacytic lymphoma; marginal zone lymphoma, for example, splenic marginal zone B-cell lymphoma (+/− villous lymphocytes), nodal marginal zone lymphoma (+/− monocytoid B-cells), and mucosa-associated lymphoid tissue (MALT) type extranodal marginal zone B-cell lymphoma; hairy cell leukemia; plasma cell myeloma/plasmacytoma; follicular lymphoma; follicle center lymphoma; mantle cell lymphoma; diffuse large B-cell lymphoma (including mediastinal large B-cell lymphoma, intravascular large B-cell lymphoma, and primary effusion lymphoma); and Burkitt lymphoma/Burkitt cell lymphoma.

In addition, the lymphoma may be selected from multiple myeloma (MM), non-Hodgkin' lymphoma (NHL), mantle cell lymphoma (MCL), follicular lymphoma, Waldenstrom macroglobulinemia (WM), B-cell lymphoma, and diffuse large B-cell lymphoma (DLBCL).

The liver disease of the present invention may be selected from the group consisting of non-alcoholic fatty liver disease (NAFLD), non-alcoholic steatohepatitis (NASH), hepatic steatosis, hepatocirrhosis, hepatitis, hepatic adenoma, insulin hypersensitivity, and liver cancer.

The liver cancer may be, for example, a liver tumor, hepatocellular adenoma, or hepatocellular carcinoma.

The autoimmune disease may be selected from the group consisting of allergic rhinitis, asthma, chronic obstructive pulmonary disease (COPD), and rheumatoid arthritis.

The present invention also provides a method of preparing a compound represented by Formula 1 below, wherein the method comprises:

reacting a compound represented by Formula 2 below with a compound represented by Formula 3 below to prepare a compound represented by Formula 4 below;

deprotecting the compound of Formula 4 to prepare a compound represented by Formula 5 below; and reacting a compound represented by Formula 5 below with a compound represented by Formula 6 to prepare the compound represented by Formula 1.

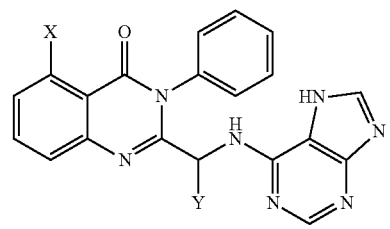

[Formula 1]

wherein, in Formula 1,
X is —H, halo, —CH$_3$, or —NH$_2$; and
Y is C$_{1-2}$ linear alkyl or C$_{3-4}$ cycloalkyl.

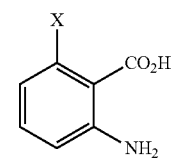

[Formula 2]

wherein, in Formula 2,
X is —H, halo, —CH$_3$, or —NH$_2$.

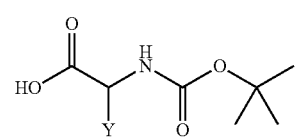

[Formula 3]

wherein, in Formula 3,
Y is C$_{1-2}$ linear alkyl or C$_{3-4}$ cycloalkyl.

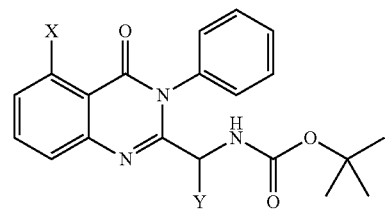

[Formula 4]

wherein, in Formula 4,
X is —H, halo, —CH$_3$, or —NH$_2$; and
Y is C$_{1-2}$ linear alkyl or C$_{3-4}$ cycloalkyl.

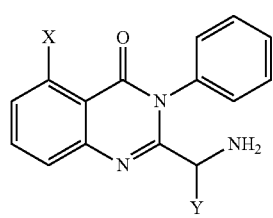

[Formula 5]

wherein, in Formula 5,
X is —H, halo, —CH$_3$, or —NH$_2$; and
Y is C$_{1-2}$ linear alkyl or C$_{3-4}$ cycloalkyl.

[Formula 6]

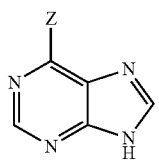

wherein, in Formula 6,
Z is halo.

Step 1 is a process of preparing the compound represented by Formula 4 by reacting the compound represented by Formula 2 with the compound represented by Formula 3.

For example, triphenyl phosphite may be added to a solution in which the compound represented by Formula 2 and the compound represented by Formula 3 are mixed together in the presence of a pyridine solvent while being stirred at room temperature.

At this time, the temperature is not particularly limited, but the mixture may be stirred at a temperature of 30° C. to 100° C., preferably 45° C. to 80° C., and more preferably 55° C. to 60° C.

The stirring time is not particularly limited, but the stirring process may be performed for 5 hours to 20 hours, preferably 8 hours to 16 hours, and more preferably 10 hours to 14 hours.

Subsequently, aniline may be added to allow a reaction to occur. At this time, the temperature is not particularly limited, but the reaction may occur at a temperature of 50° C. to 200° C., preferably 90° C. to 150° C., and more preferably 100° C. to 120° C.

At this time, reaction time is not particularly limited, but the reaction may occur for 1 hour to 20 hours, preferably 3 hours to 15 hours, and more preferably 5 hours to 10 hours.

Step 2 is a process of preparing the compound represented by Formula 5 by deprotecting the compound represented by Formula 4.

For example, the compound represented by Formula 5 may be prepared as follows: The compound represented by Formula 4 is added to a dichloromethane solution in which trifluoroacetic acid ($CF_3COOH$) is dissolved, and then reacted at room temperature for 0.1 hour to 2 hours, preferably 0.2 hour to 1.5 hours, and more preferably 0.5 hour to 1 hour.

Step 3 is a process of preparing the compound represented by Formula 1 by reacting the compound represented by Formula 5 with the compound represented by Formula 6.

For example, the compound represented by Formula 5 is added to tert-butanol, N,N-diisopropylethylamine is added thereto, and then the compound represented by Formula 6 is added to the resulting solution, and the reaction solution may be stirred while refluxing for 10 hours to 48 hours, preferably 15 hours to 30 hours, and more preferably 20 hours to 26 hours.

The present invention provides a health functional food for preventing or alleviating a blood tumor or a liver disease, including a novel quinazolinone compound or a pharmaceutically acceptable salt thereof as an active ingredient.

The health functional food may be prepared in the form of, but is not limited to, various types of beverages, gums, tea, confectioneries, vitamin complexes, and health supplements.

Hereinafter, the present invention will be described in detail with reference to examples and experimental examples.

However, these examples and experimental examples are provided for illustrative purposes only, and are not intended to limit the scope of the present invention.

<Example 1> Preparation of (S)-2-(((7H-purin-6-yl)amino)(cyclopropyl)methyl)-5-fluoro-3-phenylquinazolin-4(3H)-one (Formula 7)

[Reaction Scheme 1]

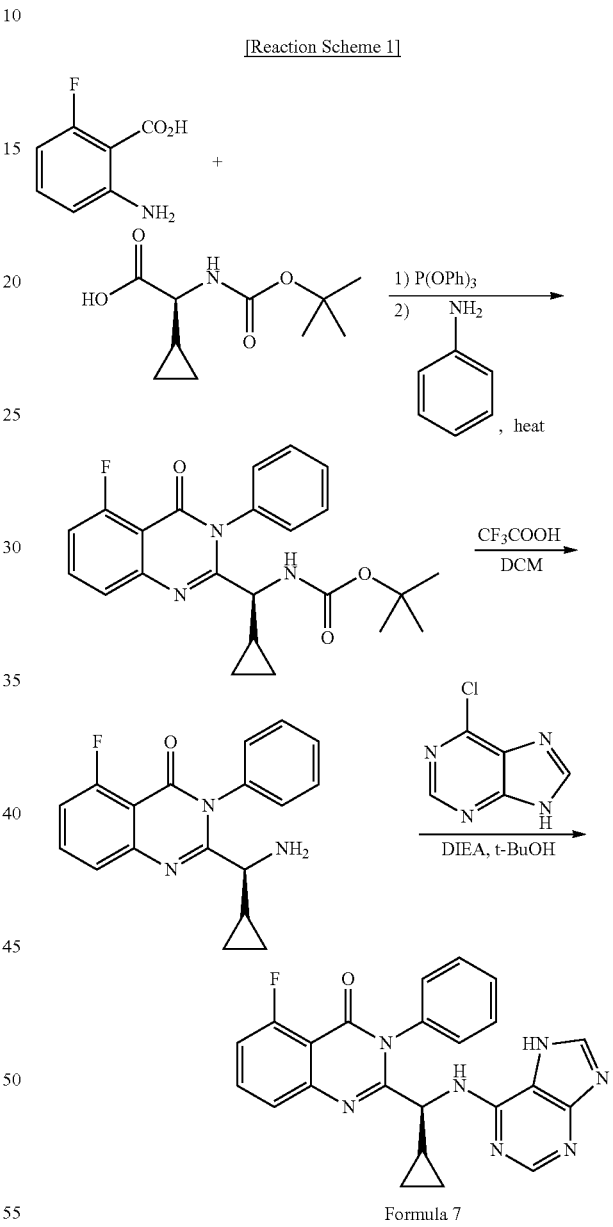

Formula 7

Step 1: Preparation of (S)-tert-butyl cyclopropyl(5-fluoro-4-oxo-3-phenyl-3,4-dihydroquinazolin-2-yl)methylcarbamate Triphenyl phosphite (1.4 eq) was added to a solution, in which 2-amino-6-fluorobenzoic acid (1.0 eq) and (S)-2-(tert-butoxycarbonylamino)-2-cyclopropylacetic acid (1.0 eq) were mixed in a pyridine solvent, while the solution was stirred at room temperature. The resulting mixture was stirred at 55° C. to 60° C. for 12 hours. Aniline (1.4 eq) was added thereto and then reacted around 110° C. for 7 hours. Thereafter, the mixed reaction solution was cooled to room temperature and extracted with ethyl acetate and water. The obtained organic layer was dehydrated with anhydrous magnesium sulfate (MgSO₄) and concentrated under reduced pressure. n-Heptane was added to the residue, followed by stirring for 30 minutes to precipitate a solid, the solid was filtered and washed with n-heptane, and then the resulting solid was dried to give (S)-tert-butyl cyclopropyl(5-fluoro-4-oxo-3-phenyl-3,4-dihydroquinazolin-2-yl)methylcarbamate with a yield of 65% to 80%.

$^1$H NMR (300 MHz, CDCl₃): δ 7.66-7.73 (m, 1H), 7.50-7.61 (m, 4H), 7.32-7.40 (m, 2H), 7.09-7.15 (t, J=18 Hz, 1H), 5.53-5.56 (d, J=9 Hz, 1H), 4.18-4.23 (t, J=15 Hz, 1H), 1.42 (s, 9H), 1.08-1.16 (m, 1H), 0.38-0.42 (m, 2H), 0.24-0.30 (m, 1H), 0.01-0.11 (m, 1H).

Step 2: Preparation of (S)-2-(amino(cyclopropyl) methyl)-5-fluoro-3-phenylquinazolin-4(3H)-one Trifluoroacetic acid (about 8 times the weight of (S)-tert-butyl cyclopropyl(5-fluoro-4-oxo-3-phenyl-3,4-dihydroquinazolin-2-yl)methylcarbamate) was added to a dichloromethane solution (about 15 times the weight of (S)-tert-butyl cyclopropyl(5-fluoro-4-oxo-3-phenyl-3,4-dihydroquinazolin-2-yl)methylcarbamate), in which (S)-tert-butyl cyclopropyl(5-fluoro-4-oxo-3-phenyl-3,4-dihydroquinazolin-2-yl)methylcarbamate was dissolved. The reaction solution was stirred at room temperature for about 0.5 hour to about 1 hour, and then pH of the reaction solution was adjusted to about 7 using an aqueous sodium carbonate solution. The dichloromethane solution was separated, dehydrated using magnesium sulfate (MgSO₄) and filtered, and magnesium sulfate (MgSO₄) was removed and then the filtrate was concentrated under reduced pressure to give (S)-2-(amino(cyclopropyl)methyl)-5-fluoro-3-phenylquinazolin-4(3H)-one with a yield of 80% to 95%.

$^1$H NMR (400 MHz, CDCl₃): δ 7.66-7.71 (m, 1H), 7.47-7.57 (m, 4H), 7.27-7.31 (m, 2H), 7.08-7.12 (t, J=16 Hz, 1H), 2.97-2.99 (d, J=8 Hz, 1H), 1.87 (s, 2H), 1.22-1.31 (m, 1H), 0.39-0.53 (m, 2H), 0.01-0.15 (m, 2H).

Step 3: Preparation of (S)-2-(((7H-purin-6-yl) amino)(cyclopropyl) methyl)-5-fluoro-3-phenylquinazolin-4(3H)-one The (S)-2-(amino(cyclopropyl)methyl)-5-fluoro-3-phenylquinazolin-4(3H)-one obtained in step 2 was added to tert-butanol (about 15 times the weight of (S)-2-(amino(cyclopropyl)methyl)-5-fluoro-3-phenylquinazolin-4(3H)-one), N, N-diisopropylamine (about 2 equivalents of (S)-2-(amino(cyclopropyl)methyl)-5-fluoro-3-phenylquinazolin-4(3H)-one) and 6-bromo-9H-purine were added thereto, and then the reaction solution was stirred while refluxing for 24 hours.

The reaction mixture was cooled, and concentrated under reduced pressure to remove tert-butanol. Ethyl acetate was added to the concentrate and sequentially washed with a diluted hydrochloric acid solution and a diluted potassium carbonate solution. The ethyl acetate layer was dehydrated with anhydrous magnesium sulfate (MgSO₄) and filtered, and the filtrate was concentrated under reduced pressure, to give (S)-2-(((7H-purine-6-yl)amino)(cyclopropyl)methyl)-5-fluoro-3-phenylquinazoline-4(3H)-one (Formula 7) in the form of solid with a yield of 60% to 80%.

$^1$H NMR (300 MHz, CDCl₃): δ 13.02 (s, 1H), 8.03 (s, 1H), 7.98 (s, 1H), 7.50-7.71 (m, 6H), 7.39-7.42 (dd, J=9 Hz, 1H), 7.08-7.14 (t, J=18 Hz, 1H), 6.76-6.79 (d, J=9 Hz, 1H), 4.93 (br s, 1H), 1.72 (br s, 1H), 1.33-1.44 (m, 1H), 0.49-0.53 (m, 2H), 0.37-0.46 (m, 1H), 0.21-0.27 (m, 1H).

ES I-MS m/z 428.45 [M+H]+

<Example 2> Preparation of (S)-2-(((7H-purin-6-yl) amino) (cyclopropyl)methyl)-5-methyl-3-phenylquinazolin-4(3H)-one (Formula 8)

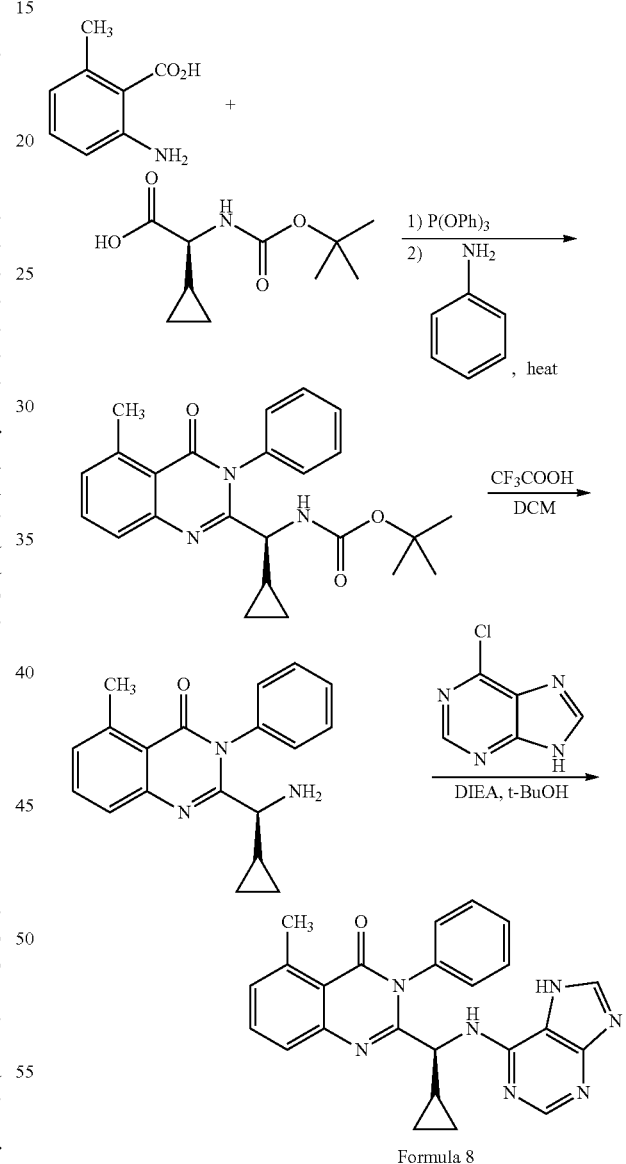

Formula 8

Step 1: Preparation of (S)-tert-butyl cyclopropyl(5-methyl-4-oxo-3-phenyl-3,4-dihydroquinazolin-2-yl) methylcarbamate (S)-tert-butyl cyclopropyl(5-methyl-4-oxo-3-phenyl-3,4-dihydroquinazolin-2-yl)methylcarbamate was prepared in the same manner as in Example 1, except that 2-amino-6-methylbenzoic acid was used instead of 2-amino-6-fluorobenzoic acid.

$^1$H NMR (400 MHz, CDCl$_3$): δ 8.33 (br.s., 3H), 7.50 (d, 4H, J=7.9 Hz), 7.28 (t, 11H, J=7.7 Hz), 7.07 (t, 2H, J=7.3 Hz), 5.35 (br. s., 1H), 3.61 (br. s., 3H), 1.32-1.51 (m, 12H), 1.17-1.30 (m, 1H), 0.51-0.73 (m, 4H), 0.47 (td, 3H, J=4.7, 9.6 Hz).

Step 2: Preparation of (S)-2-(amino(cyclopropyl)methyl)-5-methyl-3-phenyl)quinazolin-4(3H)-one (S)-2-(amino(cyclopropyl)methyl)-5-methyl-3-phenylquinazolin-4(3H)-one was prepared in the same manner as in Example 1.

$^1$H NMR (400 MHz, DMSO-d$_6$): δ 8.41 (br.s., 2H), 7.79 (t, 1H, J=7.7 Hz), 7.54-7.73 (m, 2H), 7.31-7.46 (m, 1H), 2.74 (s, 3H), 1.23 (br.s., 1H), 1.18 (tt, 1H, J=4.4, 8.7 Hz), 0.51 (s, 1H), 0.32-0.41 (m, 1H, J=4.8, 10, 10 Hz).

Step 3: Preparation of (S)-2-(((7H-purin-6-yl)amino)(cyclopropyl) methyl)-5-methyl-3-phenylquinazolin-4(3H)-one (S)-2-(((7H-purin-6-yl)amino)(cyclopropyl)methyl)-5-methyl-3-phenylquinazolin-4(3H)-one (Formula 8) was prepared in the same manner as in Example 1, except that (S)-2-(amino(cyclopropyl)methyl)-5-methyl-3-phenylquinazolin-4(3H)-one was used instead of (S)-2-(amino(cyclopropyl)methyl)-5-fluoro-3-phenylquinazolin-4(3H)one.

$^1$H NMR (400 MHz, CDCl$_3$): δ 8.29 (s, 1H), 7.96 (br.s., 1H), 7.36-7.71 (m, 7H), 7.19-7.25 (m, 1H), 6.83 (d, 1H, J=6.6 Hz), 4.96 (t, 1H, J=8.1 Hz), 2.82 (s, 3H), 1.24-1.43 (m, 2H), 0.29-0.67 (m, 3H), 0.24 (s, 1H), 0.07 (s, 1H).

ESI-MS m/z 424.48 [M+H]+

<Example 3> Preparation of (S)-2-(((7H-purin-6-yl)amino) (cyclopropyl)methyl)-5-amino-3-phenylquinazolin-4(3H)-one (Formula 9)

[Reaction Scheme 3]

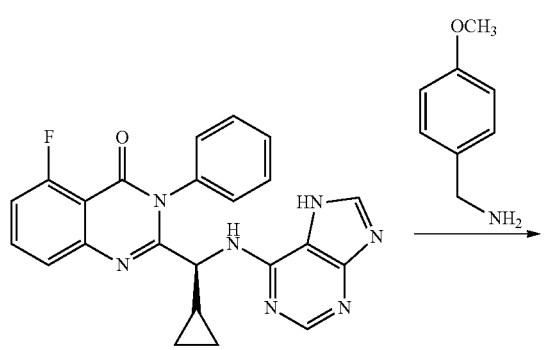

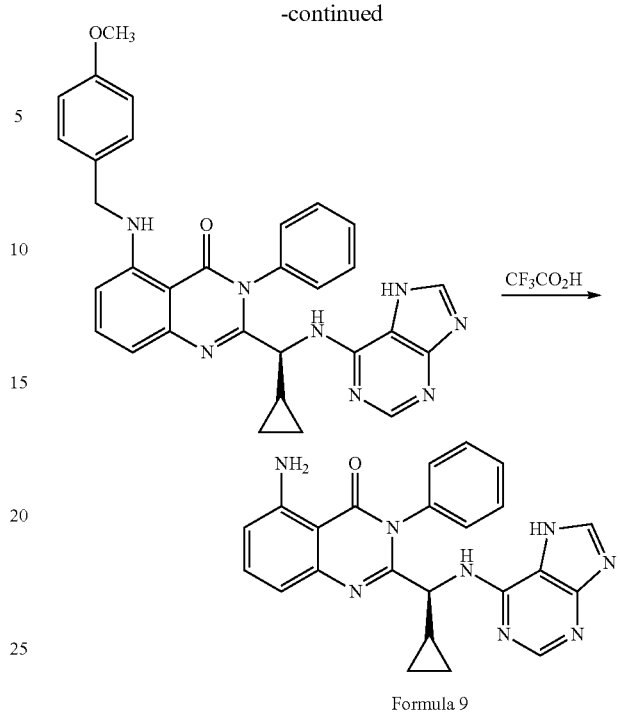

Formula 9

Step 1: Preparation of (S)-2-(((7H-purin-6-yl)amino)(cyclopropyl) methyl)-5-((4-methoxybenzyl)amino)-3-phenylquinazolin-4(3H)-one To a sealed tube in which a solution prepared by sequentially adding the (S)-2-(((7H-purin-6-yl)amino)(cyclopropyl)methyl)-5-fluoro-3-phenylquinazolin-4(3H)-one (1.0 eq.) prepared in Example 1 and triethylamine (5.0 eq.) to ethanol (15 times the volume of triethylamine) was accommodated, 4-methoxybenzylamine was further added.

Subsequently, the tube was replaced with nitrogen and sealed, and then the reaction mixture was heated to 180° C. and reacted for one day. After cooling to room temperature, the ethanol solvent was removed under reduced pressure. Thereafter, a crude mixture was subjected to silica gel column chromatography (dichloromethane/methanol 20:1) to give (S)-2-(((7H-purin-6-yl)amino)(cyclopropyl)methyl)-5-((4-methoxybenzyl)amino)-3-phenylquinazolin-4(3H)-one as yellow solid (yield: 38%).

$^1$H NMR (300 MHz, CDCl$_3$): δ 13.67 (s, 1H), 8.80-8.84 (t, J=12 Hz, 1H), 8.31 (s, 1H), 7.96 (s, 1H), 7.52-7.62 (m, 4H), 7.39-7.48 (m, 2H), 7.23-7.25 (d, J=6 Hz, 2H), 6.84-6.92 (t, J=24 Hz, 2H), 6.80-6.84 (d, J=12 Hz, 2H), 6.46-6.49 (d, J=9 Hz, 1H), 4.92 (s, 1H), 4.31-4.33 (d, J=6 Hz, 2H), 3.76 (s, 3H), 1.37-1.39 (m, 1H), 0.43-0.50 (m, 2H), 0.38-0.40 (m, 1H), 0.20-0.25 (m, 1H).

Step 2: Preparation of (S)-2-(((7H-purin-6-yl)amino)(cyclopropyl) methyl)-5-amino-3-phenylquinazolin-4(3H)-one To a solution in which (S)-2-(((7H-purin-6-yl)amino)(cyclopropyl)methyl)-5-(4-methoxybenzylamino)-3-phenylquinazolin-4(3H)-one (1.0 eq.) was dissolved in dichloromethane (6 times the volume of (S)-2-(((7H-purin-6-yl)amino)(cyclopropyl)methyl)-5-(4-methoxybenzylamino)-3-phenylquinazolin-4(3H)-one), trifluoroacetic acid (2 times the volume of dichloromethane) was added, and the resulting solution was stirred at room temperature for 0.5 hour to 2 hours. Thereafter, the pH of a crude mixture was adjusted to 7 with a 1M NaOH solution at 0° C. The resulting solution was extracted three times with dichloromethane, and the combined organic phases were dehydrated with anhydrous magnesium sulfate (MgSO$_4$) and concentrated under reduced pressure. The residue was purified by silica gel column chromatography to obtain (S)-2-(((7H-purin-6-yl)amino)(cyclopropyl)methyl)-5-amino-3-phenylquinazolin-4(3H)-one (Formula 9) as ivory solid (yield: 21%).

$^1$H NMR (300 MHz, CDCl$_3$): δ 13.16 (s, 1H), 8.30 (s, 1H), 7.97 (s, 1H), 7.53-7.64 (m, 4H), 7.40-7.45 (t, J=15 Hz, 2H), 6.92-6.95 (d, J=9 Hz, 1H), 6.84-6.86 (d, J=6 Hz, 1H), 6.54-6.56 (d, J=6 Hz, 1H), 6.15 (s, 2H), 4.93 (s, 1H), 1.32-1.41 (m, 1H), 0.47-0.48 (m, 2H), 0.38-0.43 (m, 1H), 0.22-0.25 (m, 1H).

<Example 4> Preparation of (S)-2-(1-((7H-purin-6-yl)amino)ethyl)-5-amino-3-phenylquinazolin-4(3H)-one (Formula 10)

[Reaction Scheme 4]

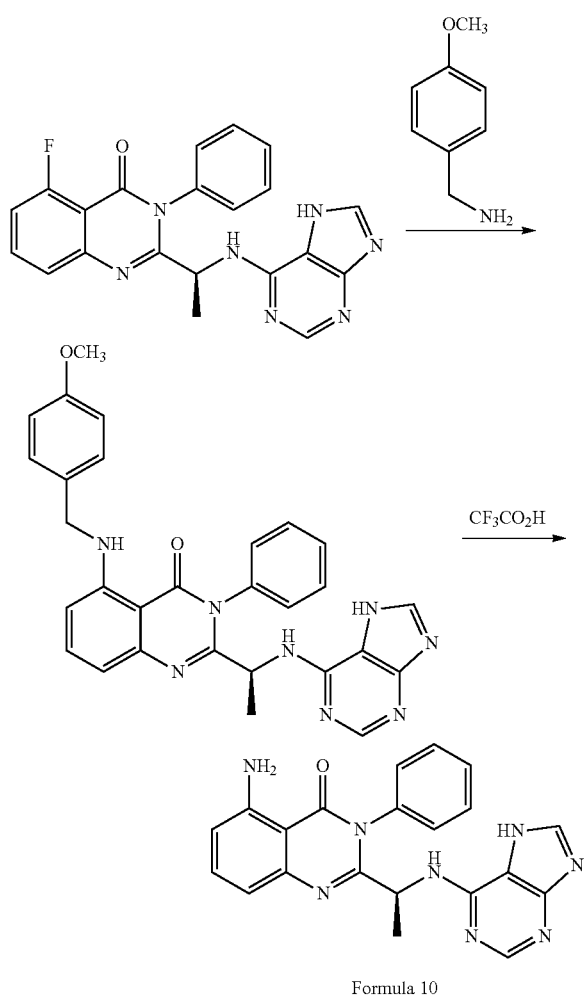

Formula 10

(S)-2-(1-((7H-purin-6-yl)amino)ethyl)-5-amino-3-phenylquinazolin-4(3H)-one (Formula 10) was prepared in the same manner as in Example 3, except that (S)-2-(1-((7H-purin-6-yl)amino)ethyl)-5-fluoro-3-phenylquinazolin-4(3H)-one was used instead of (S)-2-(((7H-purin-6-yl)amino)(cyclopropyl)methyl)-5-fluoro-3-phenylquinazolin-4(3H)-one.

$^1$H NMR (500 MHz, DMSO-d$_6$): δ 8.00-8.22 (m, 1H), 7.32-7.78 (m, 4H), 7.06 (br.s., 1H), 6.55-6.70 (m, 1H), 1.99 (s, 1H), 1.06-1.55 (m, 4H), 0.70-0.93 (m, 2H).

<Example 5> Preparation of (S)-2-(1-(7H-purin-6-ylamino)propyl)-5-amino-3-phenylquinazolin-4(3H)-one (Formula 11)

[Reaction Scheme 5]

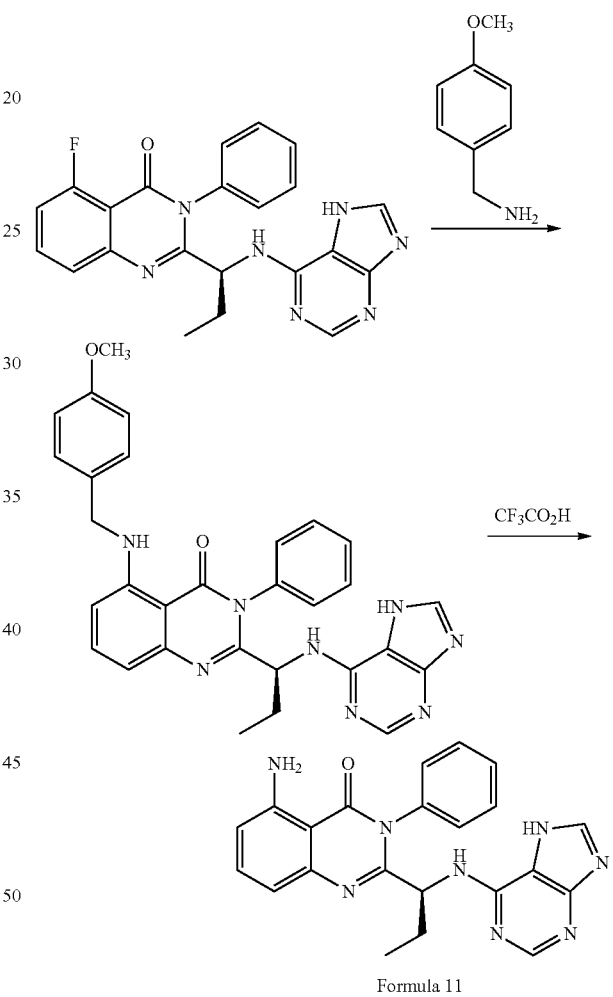

Formula 11

(S)-2-(1-((7H-purin-6-yl)amino)propyl)-5-amino-3-phenylquinazolin-4(3H)-one (Formula 11) was prepared in the same manner as in Example 3, except that (S)-2-(1-((7H-purin-6-yl)amino)propyl)-5-fluoro-3-phenylquinazolin-4(3H)-one was used instead of (S)-2-(((7H-purin-6-yl)amino)(cyclopropyl)methyl)-5-fluoro-3-phenylquinazolin-4(3H)-one.

$^1$H NMR (300 MHz, CDCl$_3$): δ 8.31 (s, 1H), 7.97 (s, 1H), 7.35-7.68 (m, 6H), 6.91-6.94 (d, J=9 Hz, 1H), 6.82-6.84 (d, J=6 Hz, 1H), 6.53-6.56 (d, J=9 Hz, 1H), 6.15 (s, 2H), 5.16 (s, 1H), 1.91-2.05 (m, 1H), 1.74-1.84 (m, 1H), 0.84-0.89 (t, J=15 Hz, 3H).

<Example 6> Preparation of (S)-2-(((7H-purin-6-yl) amino) (cyclopropyl)methyl)-5-chloro-3-phenylquinazolin-4(3H)-one (Formula 12)

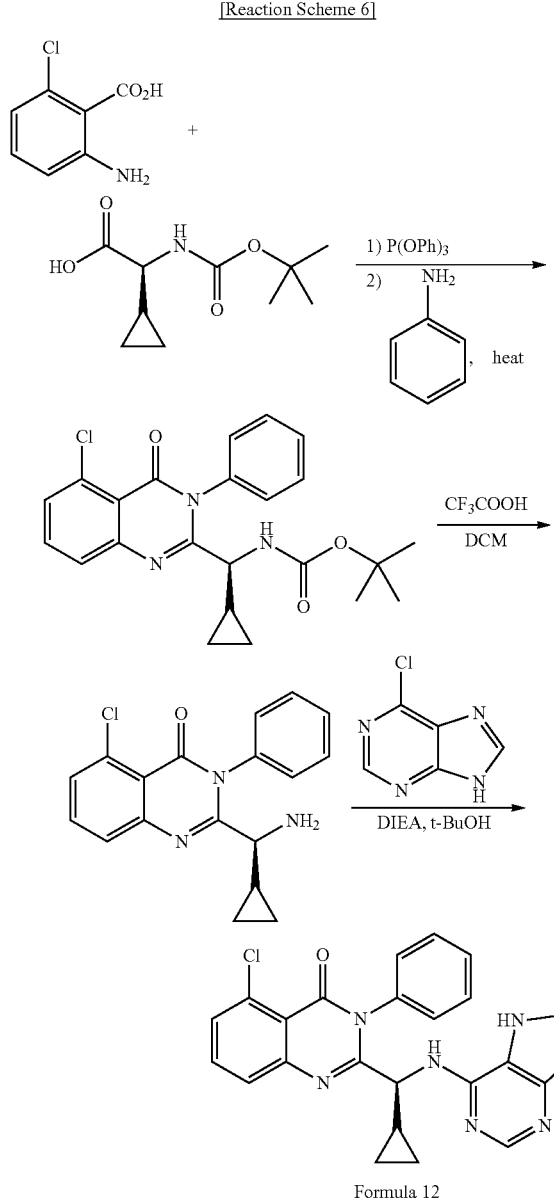

Formula 12

Step 1: Preparation of (S)-tert-butyl (5-chloro-4-oxo-3-phenyl-3,4-dihydroquinazolin-2-yl)(cyclopropyl)methylcarbamate (S)-tert-butyl (5-chloro-4-oxo-3-phenyl-3,4-dihydroquinazolin-2-yl)(cyclopropyl)methylcarbamate was prepared in the same manner as in Example 1, except that 2-amino-6-chlorobenzoic acid was used instead of 2-amino-6-fluorobenzoic acid.

Step 2: Preparation of (S)-2-(amino(cyclopropyl)methyl)-5-chloro-3-phenylquinazolin-4(3H)-one (S)-2-(amino(cyclopropyl)methyl)-5-chloro-3-phenylquinazolin-4(3H)-one was prepared in the same manner as in Example 1.

Step 3: Preparation of (S)-2-(((7H-purin-6-yl) amino)(cyclopropyl) methyl)-5-chloro-3-phenylquinazolin-4(3H)-one (S)-2-(((7H-purin-6-yl)amino)(cyclopropyl)methyl)-5-chloro-3-phenylquinazolin-4(3H)-one (Formula 12) was prepared in the same manner as in Example 1, except that (S)-2-(amino(cyclopropyl)methyl)-5-chloro-3-phenylquinazolin-4(3H)-one was used instead of (S)-2-(amino(cyclopropyl)methyl)-5-fluoro-3-phenylquinazolin-4(3H)-one.

$^1$H NMR (300 MHz, CDCl$_3$): δ 13.02 (s, 1H), 8.02 (s, 1H), 7.98 (s, 1H), 7.15-7.68 (m, 8H), 6.76-6.79 (d, J=9 Hz, 1H), 4.93 (br.s., 1H), 1.72 (br.s., 1H), 1.33-1.44 (m, 1H), 0.49-0.53 (m, 2H), 0.37-0.46 (m, 1H), 0.21-0.27 (m, 1H).

ESI-MS m/z 444.40 [M+H]+

<Example 7> Preparation of (S)-2-(((7H-purin-6-yl) amino) (cyclobutyl)methyl)-5-flouro-3-phenylquinazolin-4(3H)-one (Formula 13)

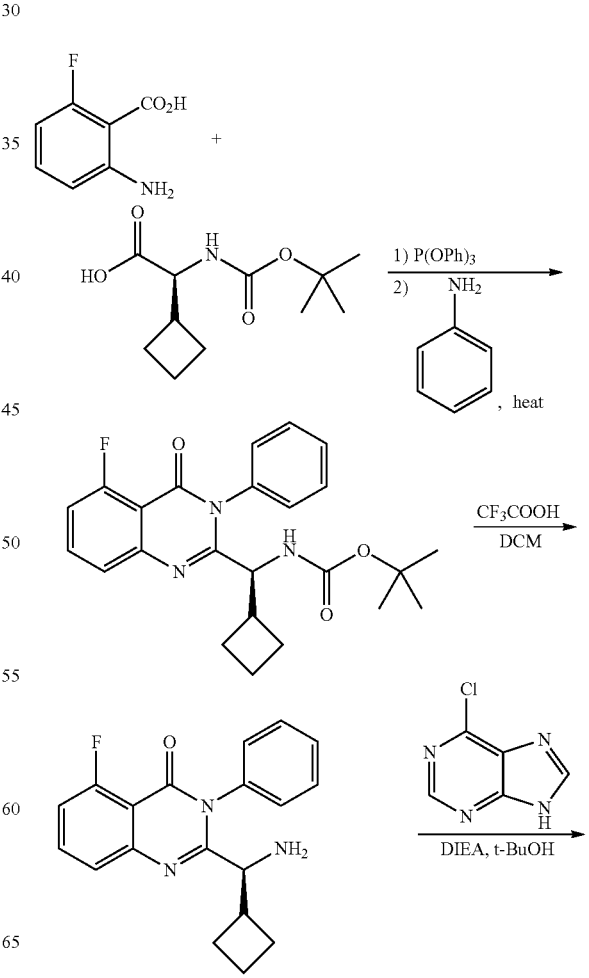

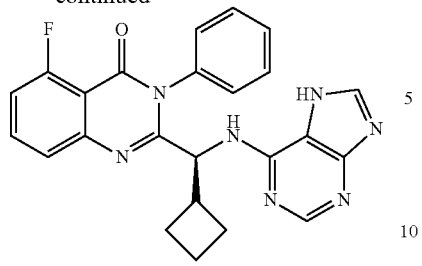

Formula 13

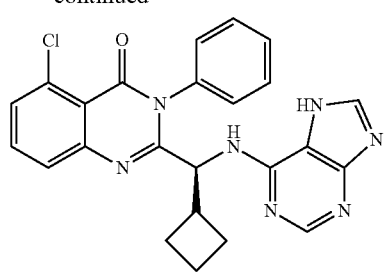

Formula 14

(S)-2-(((7H-purin-6-yl)amino)(cyclobutyl)methyl)-5-flouro-3-phenylquinazolin-4(3H)-one (Formula 13) was prepared in the same manner as in Example 1, except that (S)-2-(tert-butoxycarbonylamino)-2-cyclobutylacetic acid was used instead of (S)-2-(tert-butoxycarbonylamino)-2-cyclopropylacetic acid.

$^1$H NMR (300 MHz, DMSO-d$_6$): δ 12.95 (s, 1H), 8.13 (br.s., 1H), 7.85 (br.s., 1H), 7.24-7.60 (m, 8H), 5.18 (br.s., 1H), 3.05 (br.s., 1H), 1.64-2.01 (m, 7H).

<Example 8> Preparation of (S)-2-(((7H-purin-6-yl)amino) (cyclobutyl)methyl)-5-chloro-3-phenylquinazolin-4(3H)-one (Formula 14)

(S)-2-(((7H-purin-6-yl)amino)(cyclobutyl)methyl)-5-chloro-3-phenylquinazolin-4(3H)-one (Formula 14) was prepared in the same manner as in Example 1, except that 2-amino-6-chlorobenzoic acid was used instead of 2-amino-6-fluorobenzoic acid, and (S)-2-(tert-butoxycarbonylamino)-2-cyclobutylacetic acid was used instead of (S)-2-(tert-butoxycarbonylamino)-2-cylcopropylacetic acid.

$^1$H NMR (300 MHz, DMSO-d$_6$): δ 12.88 (s, 1H), 8.17 (br.s., 1H), 8.00 (s, 1H), 7.12-7.87 (m, 8H), 5.18 (br.s., 1H), 3.06 (br.s., 1H), 1.62-1.99 (m, 7H)

Structures of the compounds of Formulas 7 to 14 are shown in Table 1 below.

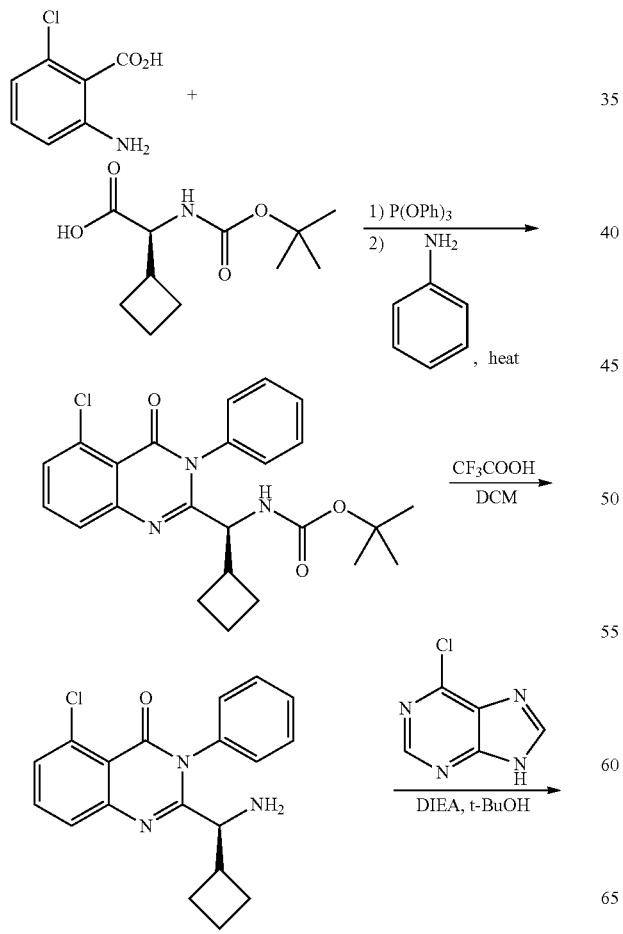

TABLE 1

| Formula | Chemical Structure |
|---|---|
| 7 | 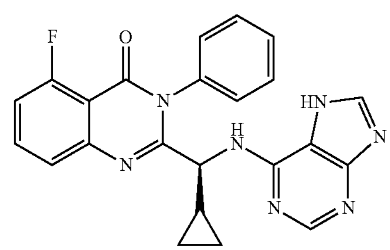 [SMILES: O=c1c2c(F)cccc2nc([C@@H](Nc2ncnc3nc[nH]c23)C2CC2)n1-c1ccccc1] |
| 8 | 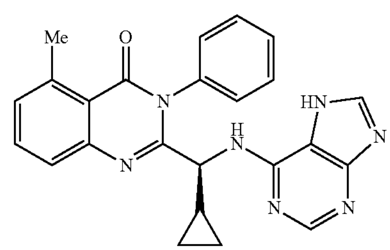 [SMILES: Cc1cccc2nc([C@@H](Nc3ncnc4nc[nH]c34)C3CC3)n(-c3ccccc3)c(=O)c12] |
| 9 | 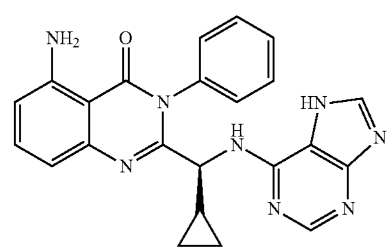 [SMILES: Nc1cccc2nc([C@@H](Nc3ncnc4nc[nH]c34)C3CC3)n(-c3ccccc3)c(=O)c12] |

TABLE 1-continued

| Formula | Chemical Structure |
|---|---|
| 10 | 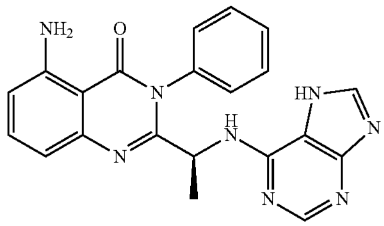 [SMILES: C[C@H](Nc1ncnc2nc[nH]c12)c1nc2cccc(N)c2c(=O)n1-c1ccccc1] |
| 11 | 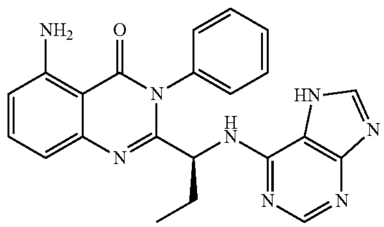 [SMILES: CC[C@H](Nc1ncnc2nc[nH]c12)c1nc2cccc(N)c2c(=O)n1-c1ccccc1] |
| 12 | 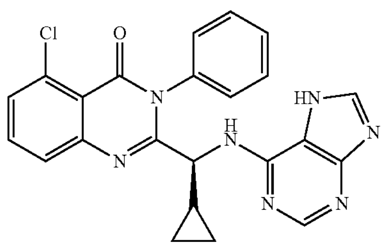 [SMILES: O=c1c2c(Cl)cccc2nc([C@@H](Nc2ncnc3nc[nH]c23)C2CC2)n1-c1ccccc1] |
| 13 | 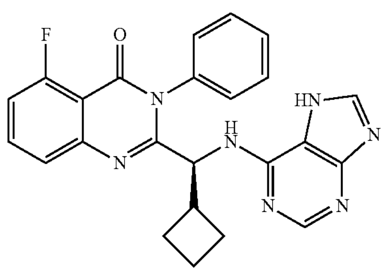 [SMILES: O=c1c2c(F)cccc2nc([C@@H](Nc2ncnc3nc[nH]c23)C2CCC2)n1-c1ccccc1] |
| 14 | 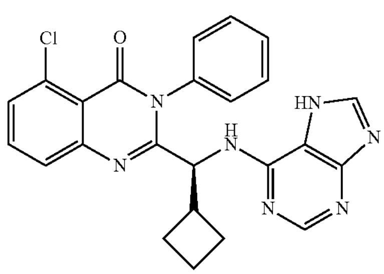 [SMILES: O=c1c2c(Cl)cccc2nc([C@@H](Nc2ncnc3nc[nH]c23)C2CCC2)n1-c1ccccc1] |

<Experimental Example 1> PI3K Kinase Activity Test (1) Experimental Method An experiment was conducted using a homogeneous, fluorescence-based immunoassay, which is Adapta kinase assay.

SelectScreen™ Services available from Thermo Fisher Scientific Inc. was carried out. A principle of the experiment is shown in FIG. 1.

(2) Experimental Results

The results of the experiment are shown in Table 2 below.

As shown in Table 2, the compound of Formula 7 and the compound of Formula 8 exhibited higher activity than the control drug, idelalisib. In particular, they exhibited specific inhibitory activity on p110δ and also exhibited excellent activity with respect to p110γ.

In particular, ratios of PI3Kα/PI3Kδ and PI3Kβ/PI3Kδ, as $IC_{50}$ values, were shown as 412 and 210 respectively in the case of the compound of Formula 7, and 1,488 and 1,800 respectively in the case of the compound of Formula 8.

In addition, it was confirmed that the compound of Formula 7 and the compound of Formula 8 have high delta (δ) selectivity. Each of them exhibited a ratio of PI3Kγ/PI3Kδ of 51 and 95 respectively, whereas idelalisib exhibited the ratio about 25.

From these results, it was confirmed that the compounds of Formulae 7 and 8 could have effective and sufficient activity with respect to delta (δ)-dependent cancers.

TABLE 2

| PI3Ks | $IC_{50}$ (nM) p110α | $IC_{50}$ (nM) p110β | $IC_{50}$ (nM) p110γ | $IC_{50}$ (nM) p110δ |
|---|---|---|---|---|
| Idelalisib | 498 | 570 | 23 | 0.9 |
| Formula 7 | 206 | 105 | 25.7 | 0.5 |
| Formula 8 | 134 | 162 | 8.6 | 0.09 |

<Experimental Example 2> Experiment for Confirming Effect on Reducing AKT(Ser473) Phosphorylation in Leukemia and Lymphoma Cell Lines (1) Experimental Method Cell lines (SUDHL 5, SUDHL 10, CCRF-SB, and MOLT4) were subjected to serum depletion for 2 hours, and then were treated with 1 μM of each of the compound of Formula 7, the compound of Formula 8, idelalisib (comparative drug 1), TGR1202 (comparative drug 2), and dimethylsulfoxide (DMSO) for 1 hour. Subsequently, cells were lysed and fractionated according to size, followed by immunoblotting with antibodies directed against Phospho-Akt (Ser473).

(2) Experimental Results

Figure 2:
FIG. 2 illustrates results of Experimental Example 2 for confirming an effect on reducing AKT (Ser473) phosphorylation in leukemia and lymphoma cell lines.
Figure 2:
Figure 2:
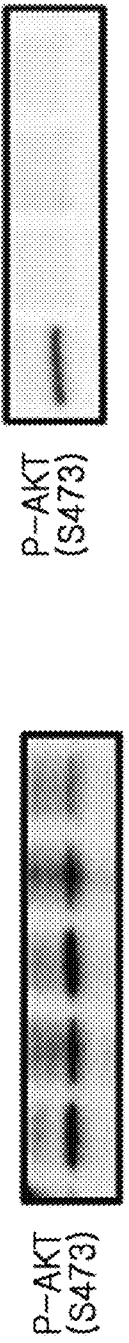
Figure 2:
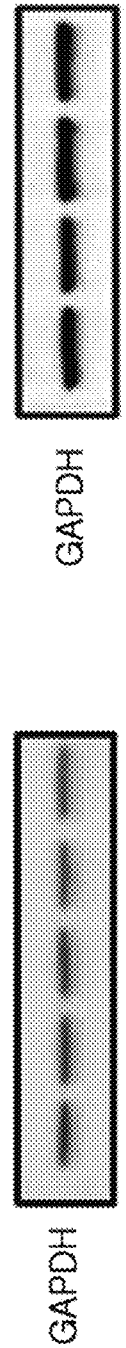

The results of the experiment are shown in FIG. 2.

As illustrated in FIG. 2, it was confirmed that the compound of Formula 7 and the compound of Formula 8 induced the reduction of AKT phosphorylation in various diffuse large B-cell lymphoma (DLBCL) and acute lymphocytic leukemia (ALL) cells.

<Experimental Example 3> Experiment for Confirming Effect on Inhibiting Growth of Leukemia and Lymphoma Cells (1) Experimental Method PI3K p110δ is highly expressed in leukemia and lymphoma cell lines, and cell growth is inhibited by suppressing PI3K p110δ.

Thus, an experiment was carried out to confirm the effects of compounds on inhibiting cell growth.

Diffuse large B-cell lymphoma (DLBCL)-derived cells and acute lymphocytic leukemia (ALL)-derived cells were cultured with the compound of Formula 7, the compound of Formula 8, or idelalisib, along with a control medium for 48 hours.

Cell growth-inhibiting effects on the DLBCL-derived cells and the ALL-derived cells were evaluated by measuring the absorbance of cell counting kit-8 (CCK-8) dye. During the last 3 hours of the 48 hours, 10 μl of a CCK-8 dye was added to each plate and then cultured.

All data are expressed as the mean (±SD) of three independent experiments.

(2) Experimental Results

Figure 3:
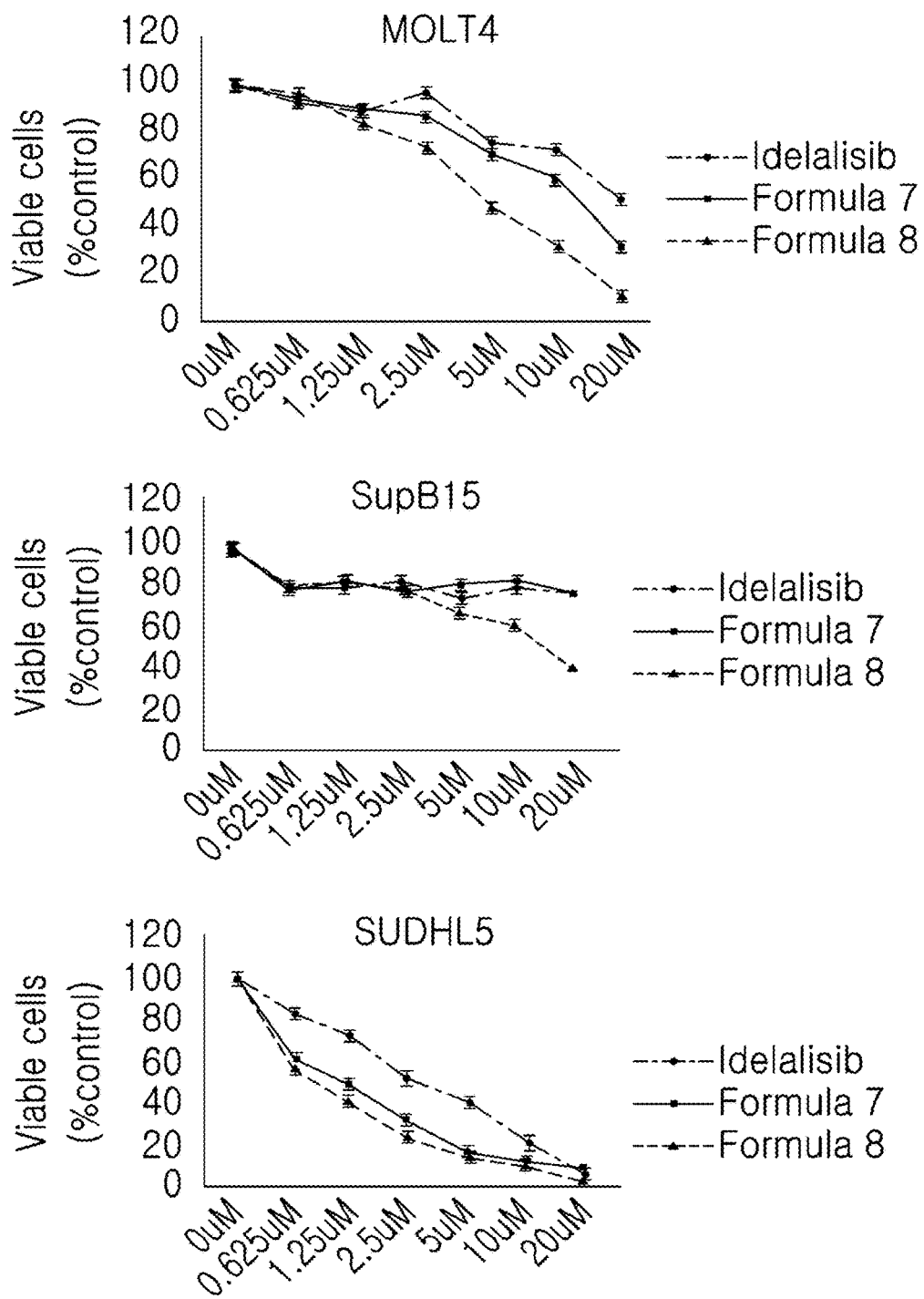
FIG. 3 illustrates results of Experimental Example 3 for confirming an inhibitory effect on the growth of leukemia and lymphoma cells.

The results of the experiment are shown in FIG. 3.

As illustrated in FIG. 3, growth of the DLBCL-derived cells and the ALL-derived cell line was reduced at a concentration ranging from 0.625 μM to 20 μM.

At this time, lethal concentration 50 ($LC_{50}$), which is the concentration of compounds being lethal to 50% of the cells, is shown in Table 3, and it was confirmed that the compound of Formula 7 and the compound of Formula 8 exhibited a lower $LC_{50}$ value than that of idelalisib.

TABLE 3

| | $LC_{50}$ (μM) | $LC_{50}$ (μM) | $LC_{50}$ (μM) |
|---|---|---|---|
| Cell line | SUDHL5 (DLBCL) | MOLT4 (ALL) | SupB15 (ALL) |
| Idelalisib | 3.0 | >20 | >20 |
| Formula 7 | 1.1 | 13.7 | >20 |
| Formula 8 | 0.9 | 4.9 | 16.53 |

<Experimental Example 4> Experiment for Confirming Effect on Apoptosis of Diffuse Large B-cell Lymphoma (DLBCL) and Acute Lymphocytic Leukemia (ALL) Cells by SDS-PAGE (1) Experimental Method $2.6 \times 10^6$ cells were cultured with idelalisib (comparative drug), the compound of Formula 7, or the compound of Formula 8 at a concentration of 50 μM for 36 hours, and then protein analysis was performed by sodium dodecyl sulfate-polyacrylamide gel electrophoresis (SDS-PAGE).

The caspase 3 and 9 PARP proteins, which are proteins involved in apoptosis, normally exist as inactive precursors (FL), and they are activated by being cleaved (CL) when receiving an apoptosis-stimulating signal. Immunoblotting analysis was performed using antibodies of these, and glyceraldehyde-3-phosphate dehydrogenase (GAPDH) was used as a loading control.

(2) Experimental Results

Figure 4:
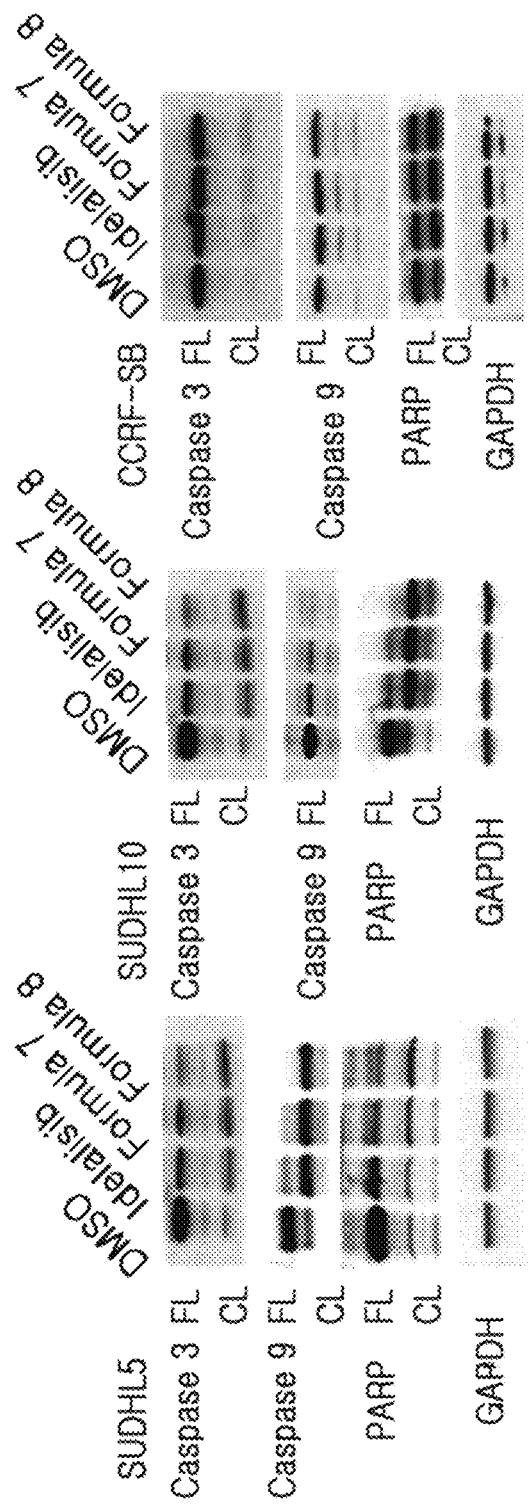
FIG. 4 illustrates SDS-PAGE analysis results of Experimental Example 4 for confirming an effect on the apoptosis of diffuse large B-cell lymphoma (DLBCL) cells and acute lymphoblastic leukemia (ALL) cells.

Results of the experiment are shown in FIG. 4.

As illustrated in FIG. 4, the compound of Formula 7 and the compound of Formula 8 induced apoptosis in diffuse large B-cell lymphoma (DLBCL) and acute lymphocytic leukemia (CLL) cells.

In addition, apoptosis occurred more actively with the compound of Formula 7 and the compound of Formula 8 than with the comparative drug (idelalisib).

From these results, it was confirmed that the compound of Formula 7 and the compound of Formula 8 inhibited cell growth through apoptosis.

<Experimental Example 5> Experiment for Confirming Effect on Apoptosis of Diffuse Large B-cell Lymphoma (DLBCL) and Acute Lymphocytic Leukemia (ALL) Cells by Flow Cytometry (1) Experimental Method $1 \times 10^6$ diffuse large B-cell lymphoma (DLBCL) cells and $1 \times 10^6$ acute lymphocytic leukemia (ALL) cells were cultured and treated with each of the comparative drug (Idelalisib), the compound of Formula 7, and the compound of Formula 8 at a concentration of 50 μM for 24 hours. The cells were washed with PBS, and then suspended in a binding buffer. 5 μl of an Annexin V-FITC stock solution (Becton Dickinson Science, Inc) and 5 μl of PI (20 μg/ml) were added thereto, followed by incubation at room temperature for 15 minutes with light-shielding, and then the target material was quantified on FACScan™ (Becton Dickinson) by flow cytometry.

(2) Experimental Results

Figure 5:
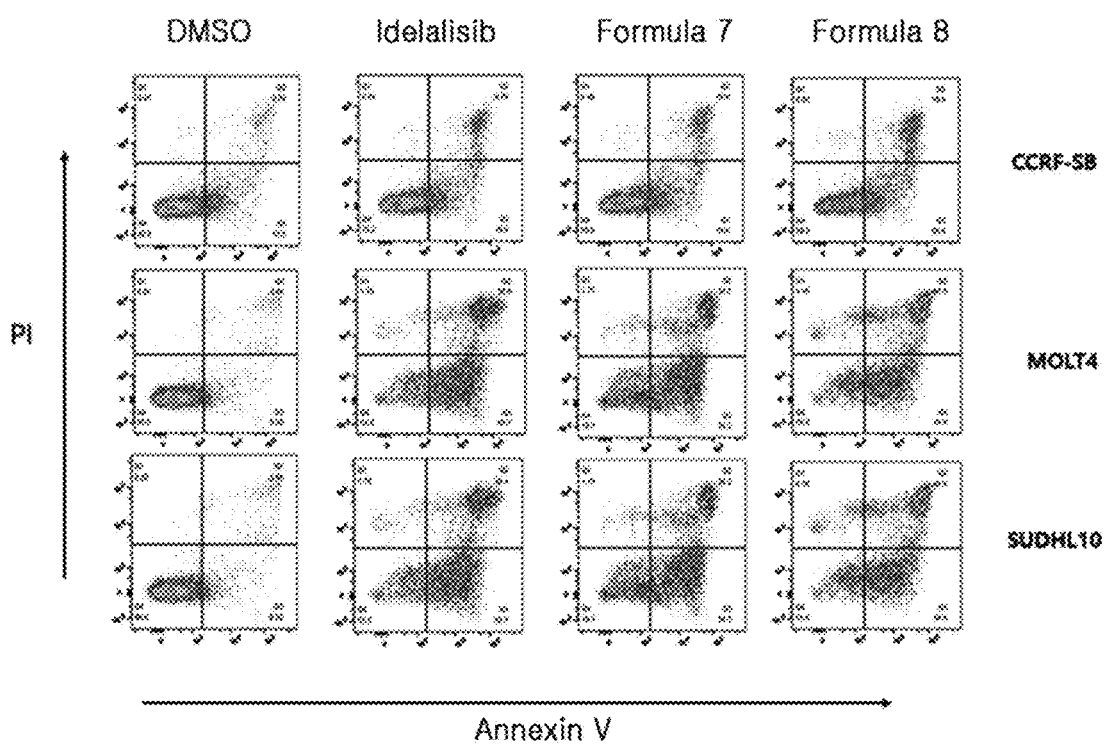
FIG. 5 illustrates flow cytometry results of Experimental Example 5 for confirming an effect on the apoptosis of diffuse large B-cell lymphoma (DLBCL) cells and acute lymphoblastic leukemia (ALL) cells.

The results of the experiment are shown in FIG. 5.

As illustrated in FIG. 5, it was confirmed that the compound of Formula 7 and the compound of Formula 8 more effectively induced apoptosis than the comparative drug (Idelalisib).

<Experimental Example 6> Experiment for Confirming Inhibitory Effect on Angiogenesis (1) Experimental Method To compare levels of angiogenesis inhibition by the compound of Formula 7, the compound of Formula 8, and a comparative drug (Idelalisib), human umbilical vein endothelial cells (HUVECs), which are vascular endothelial cells, and endothelial cell growth media were obtained from Life Technologies.

Figure 6:
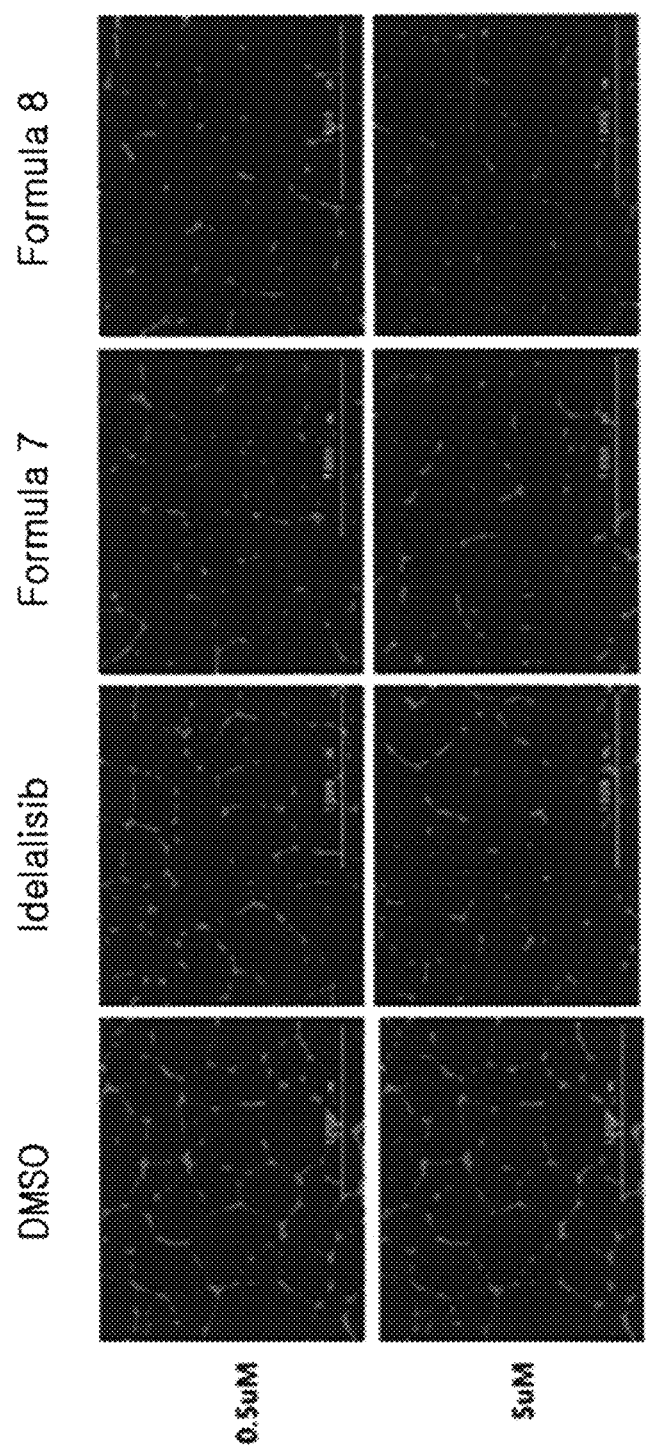
FIG. 6 illustrates Cytation™ 5 fluorescence microscopic (BioTek) images showing tube formation results of Experimental Example 6 for confirming an inhibitory effect on angiogenesis.

The human umbilical vein endothelial cells (HUVECs) were cultured along with the compound of Formula 7, the compound of Formula 8, or the comparative drug (Idelalisib) on basement membrane matrix at 37° C. After 18 hours, tube formation was photographed using a Cytation™ 5 fluorescence microscope (BioTek), and the number of areas formed by branch points was counted using software (see FIG. 6).

(2) Experimental Results

Figure 7:
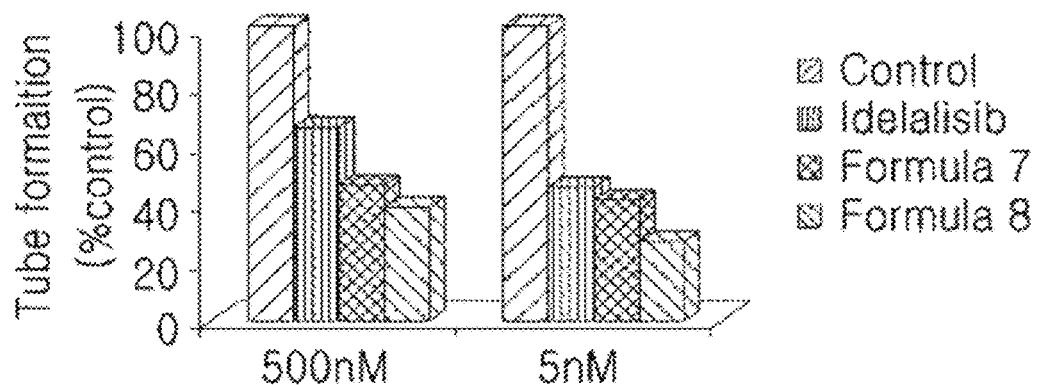
FIG. 7 is a graph showing an inhibitory effect on angiogenesis in Experimental Example 6 for confirming an inhibitory effect on angiogenesis.
Figure 8:
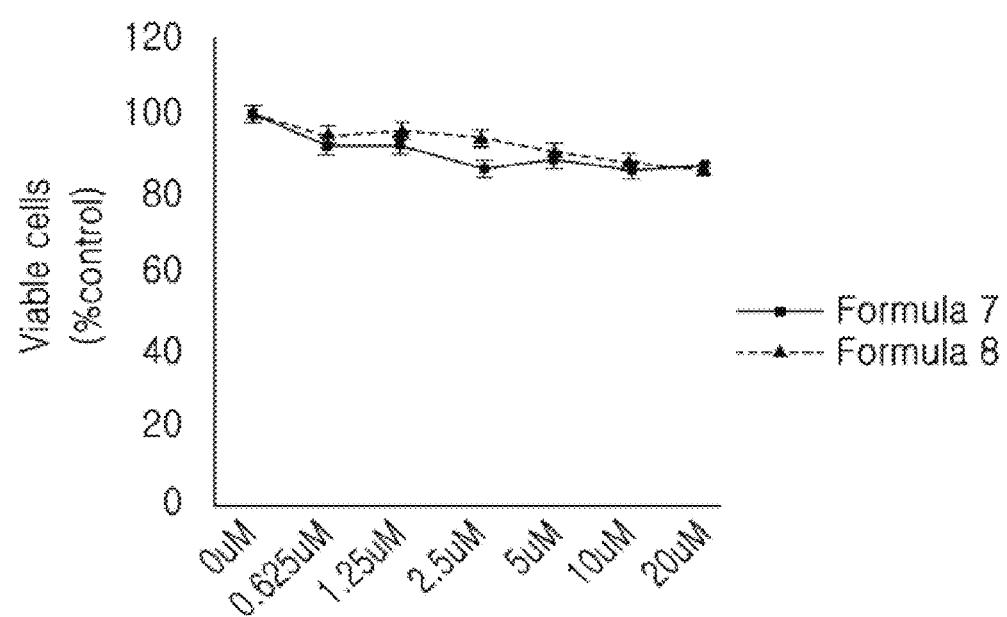
FIG. 8 is a graph showing the number of viable HUVECs treated with a compound in Experimental Example 6 for confirming an inhibitory effect on angiogenesis.

The results of the experiment are shown in FIGS. 7 and 8.

As illustrated in FIG. 7, the compound of Formula 7 and the compound of Formula 8 inhibited angiogenesis more than the comparative drug (Idelalisib) did.

In addition, as illustrated in FIG. 8, the compound of Formula 7 and the compound of Formula 8 did not significantly affect the cytotoxicity of the human umbilical vein endothelial cells (HUVECs).

<Experimental Example 7> Single Dose Toxicity Test in Rats (1) Experimental Method The compound of Formula 7 and the compound of Formula 8 were orally administered to eight six-week-old female rats, to observe the single dose oral toxicity thereof and to obtain an approximate lethal dose. The dosage was set at 10 mL/kg, and the dosage for each rat was calculated based on body weight. Each compound was administered at doses of 100 mg/kg, 300 mg/kg, 900 mg/kg, and 1,500 mg/kg, and general symptoms were observed once a day from day 1 to day 2 after administration.

(2) Experimental Results

The results of the experiment are shown in FIG. 9.

Lethal dose of compound of formula 7 is over than 1,500 mg/kg and that of compound of formula 8 is 1,500 mg/kg.

Meanwhile, the compound represented by Formula 1 according to the present invention may be formulated into various forms. Several formulation methods using the compound represented by Formula 1 according to the present invention as an active ingredient are provided below for illustrative purposes only, but are not intended to limit the present invention.

<Preparation Example 1> Formulation of Pharmaceutical Preparations 1-1. Preparation of Powder

| Compound of Formula 1 | 500 mg |
|---|---|
| Lactose | 100 mg |
| Talc | 10 mg |

The above ingredients were mixed and airtight packages were filled therewith to prepare powder.

1-2. Preparation of Tablets

| Compound of Formula 1 | 500 mg |
|---|---|
| Corn starch | 100 mg |
| Lactose | 100 mg |
| Magnesium stearate | 2 mg |

The above ingredients were mixed, and then tablets were prepared according to a general method of preparing tablets.

1-3. Preparation of Capsules

| Compound of Formula 1 | 500 mg |
|---|---|
| Corn starch | 100 mg |
| Lactose | 100 mg |
| Magnesium stearate | 2 mg |

The above ingredients were mixed, and then gelatin capsules were filled therewith according to a general method of preparing capsules to prepare capsules.

1-4. Preparation of Injections

| Compound of Formula 1 | 500 mg |
|---|---|
| Sterile distilled water for injection | appropriate amount |
| pH adjuster | appropriate amount |

According to a general method of preparing an injection, ampoules were prepared with the above ingredients included in a single ampoule (2 ml).

1-5. Preparation of Liquids

| Compound of Formula 1 | 100 mg |
|---|---|
| Isomerized sugar | 10 g |
| Mannitol | 5 g |
| Purified water | appropriate amount |

Each ingredient was added to and dissolved in purified water according to a general method of preparing a liquid. A lemon flavor was added in an appropriate amount and the above ingredients were mixed. Purified water was added thereto such that a total amount of the resulting solution is adjusted to 100 ml. A brown bottle is filled therewith, and sterilized to prepare liquids.

What is claimed:

1. A compound of Formula 1:

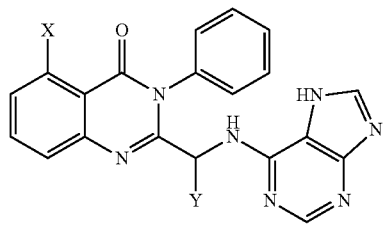

Formula 1 or a pharmaceutically acceptable salt thereof, wherein:

X is hydrogen, halo, or methyl; and

Y is $C_{3-4}$ cycloalkyl.

2. The compound of claim 1, or a pharmaceutically acceptable salt thereof, wherein:

X is fluoro; and

Y is cyclopropyl.

3. The compound of claim 1, or a pharmaceutically acceptable salt thereof, wherein:

X is methyl; and

Y is cyclopropyl.

4. The compound of claim 1, or a pharmaceutically acceptable salt thereof, wherein:

X is fluoro; and

Y is cyclobutyl.

5. The compound of claim 1, or a pharmaceutically acceptable salt thereof, wherein:

X is chloro; and

Y is cyclobutyl.

6. A pharmaceutical composition comprising a pharmaceutically acceptable excipient and a compound of Formula 1:

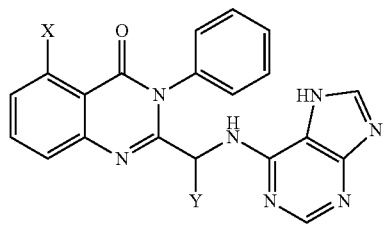

Formula 1 or a pharmaceutically acceptable salt thereof, wherein:

X is hydrogen, halo, or methyl; and

Y is $C_{3-4}$ cycloalkyl.

7. A method for inhibiting a kinase activity in a patient, comprising administering to a patient in need thereof a pharmaceutical composition comprising a pharmaceutically acceptable excipient and a compound of Formula 1:

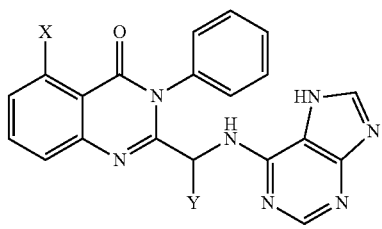

Formula 1 or a pharmaceutically acceptable salt thereof,
wherein:
X is hydrogen, halo, or methyl; and
Y is $C_{3-4}$ cycloalkyl,
wherein the kinase is at least one selected from the group consisting of phosphoinositide 3-kinase alpha, phosphoinositide 3-kinase beta, phosphoinositide 3-kinase gamma, and phosphoinositide 3-kinase delta.

8. The method of claim 7, wherein the patient has a disease selected from the group consisting of a hematological malignancy, a liver disease, and an autoimmune disease.

9. The method of claim 8, wherein the hematological malignancy is selected from the group consisting of leukemia and lymphoma.

10. The method of claim 8, wherein the liver disease is selected from the group consisting of hepatic adenoma, hepatic steatosis, hepatitis, hepatocirrhosis, insulin hypersensitivity, liver cancer, non-alcoholic fatty liver disease, and non-alcoholic steatohepatitis.

11. The method of claim 7, wherein the compound selectively inhibits phosphoinositide 3-kinase delta activity in the patient.

12. A method for treating a hematological malignancy, comprising administering to a patient in need thereof a pharmaceutical composition comprising a pharmaceutically acceptable excipient and a compound of Formula 1:

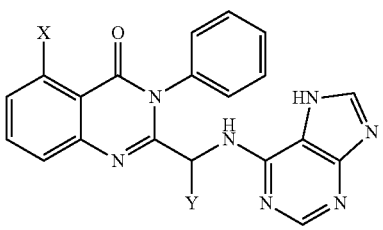

Formula 1 or a pharmaceutically acceptable salt thereof,
wherein:
X is hydrogen, halo, or methyl; and
Y is $C_{3-4}$ cycloalkyl.

13. The method of claim 12, wherein the hematological malignancy is selected from the group consisting of leukemia and lymphoma.

* * * * *